United States Patent [19]

Saita et al.

[11] Patent Number: 5,389,481
[45] Date of Patent: Feb. 14, 1995

[54] ELECTROPHOTOGRAPHIC PHOTORECEPTOR

[75] Inventors: Atsuo Saita, Machida; Shuichi Maeda, Hidaka; Kohzo Ishio; Hitoshi Ono, both of Yokohama; Tetsuo Murayama, Machida, all of Japan

[73] Assignee: Mitsubishi Kasei Corporation, Tokyo, Japan

[21] Appl. No.: 225,697

[22] Filed: Apr. 11, 1994

Related U.S. Application Data

[63] Continuation-in-part of Ser. No. 53,653, Apr. 29, 1993, abandoned.

[30] Foreign Application Priority Data

| | | |
|---|---|---|
| Apr. 30, 1992 [JP] | Japan | 4-111828 |
| Sep. 11, 1992 [JP] | Japan | 4-243701 |
| Oct. 19, 1992 [JP] | Japan | 4-280208 |
| Jan. 20, 1993 [JP] | Japan | 5-007832 |

[51] Int. Cl.$^6$ .................. G03G 5/047; G03G 5/06
[52] U.S. Cl. ................... 430/59; 430/73; 430/75; 430/83
[58] Field of Search ............ 430/59, 73, 75, 83

[56] References Cited

U.S. PATENT DOCUMENTS

| | | | |
|---|---|---|---|
| 5,089,365 | 2/1992 | Kuroda et al. | 430/75 X |
| 5,158,850 | 10/1992 | Sasaki et al. | 430/73 X |
| 5,168,025 | 12/1992 | Ono et al. | 430/59 |
| 5,284,728 | 2/1994 | Murayama et al. | 430/59 |

FOREIGN PATENT DOCUMENTS

| | | |
|---|---|---|
| 0475264 | 3/1992 | European Pat. Off. |
| 3626497 | 2/1987 | Germany |

OTHER PUBLICATIONS

Patent Abs. of Japan, vol. 7, No. 146 (P-206)(1291), Jun. 25, 1983, JP-A-58-058 551, Apr. 7, 1983.
Patent Abs. of Japan, vol. 12, No. 156, (P-701)(3003), May 13, 1988, JP-A-62-273 544, Nov. 27, 1987.

*Primary Examiner*—Roland Martin
*Attorney, Agent, or Firm*—Oblon, Spivak, McClelland, Maier & Neustadt

[57] ABSTRACT

An electrophotographic photoreceptor comprising an electrically conductive substrate and a photosensitive layer formed thereon, wherein said photosensitive layer contains an arylamine compound of the following formula (I):

$$Ar^1\text{-}N(R^3)\text{-}C_6H_3(R^1)\text{-}Y\text{-}C_6H_3(R^2)\text{-}N(R^4)\text{-}Ar^2 \quad \text{with } C_6H_4(X)\text{-}CR^5=C(R^6)(R^7) \quad (I)$$

wherein X is a hydrogen atom or a group of the formula (II):

$$-CR^8=C(R^9)(R^{10}) \quad (II)$$

Y is a group of the formula (III) or (IV):

$$-O-A^1-O- \quad (III)$$

$$-A^2-O-A^3- \quad (IV)$$

wherein, the substituents are defined hereafter.

16 Claims, 2 Drawing Sheets

ELECTROPHOTOGRAPHIC PHOTORECEPTOR

This application is a continuation-in-part application of U.S. patent application Ser. No. 08/053,653, filed on Apr. 29, 1993, now abandoned, claiming the priority dates of Apr. 30, 1992, Sep. 11, 1992, Oct. 19, 1992, and Jan. 20, 1993.

The present invention relates to an electrophotographic photoreceptor. More particularly, it relates to a highly sensitive electrophotographic photoreceptor of high performance having a photosensitive layer containing an organic photoconductive material.

Heretofore, inorganic photoconductive substances such as selenium, cadmium sulfide and zinc oxide have been widely used for photosensitive layers of electrophotographic photoreceptors. However, selenium and cadmium sulfide are required to be recovered as poisonous substances, and selenium tends to be crystallized by heat and thus is poor in the heat resistance. Cadmium sulfide and zinc oxide are poor in moisture resistance, and zinc oxide lacks in printing resistance. Therefore, efforts have been made for the development of a new photoreceptor. Recently, a research for the use of organic photoconductive materials for photosensitive layers of electrophotographic photoreceptors has found some progress, and some of them have been practically employed. As compared with inorganic materials, the organic photoconductive materials have advantages such that they are light in weight, they can easily be formed into films, preparation of photoreceptors is thereby easy, transparent photoreceptors can be produced depending upon their types, and they are free from pollution.

Recently, so-called function-separated photoreceptors wherein functions to generate electric charge carriers and to transport the generated carriers are performed by separate compounds, have been the main objects for development, since such function-separated photoreceptors are effective for high sensitivity, and organic photoreceptors of this type have been practically developed.

As a medium for transporting electric charge carriers, it is possible to employ a polymer photoconductive compound such as polyvinyl carbazole. Otherwise, it is possible to employ a low molecular weight photoconductive compound by dispersing and dissolving such a compound in a binder polymer. It is particularly convenient to use an organic low molecular weight photoconductive compound, since it is thereby possible to select as the binder a polymer excellent in the film-forming properties, the flexibility and the adhesive properties, and it is readily possible to obtain a photoreceptor excellent in the mechanical properties (see e.g. Japanese Unexamined Patent Publications No. 196767/1985, No. 218652/1985, No. 233156/1985, No. 48552/1988 and No. 267552/1989, Japanese Examined Patent Publication No. 39306/1991, and Japanese Unexamined Patent Publication No. 113459/1991, No. 123358/1991 and No. 149560/1991). However, it has been difficult to find out a compound suitable for the preparation of a highly sensitive photoreceptor.

Further, with an ever increasing demand for high sensitivity, various problems exist from the viewpoint of electrical properties such that the residual potential is inadequate, the photosensitivity is poor, or in repeated use, the chargeability deteriorates and the residual potential accumulates. To solve such problems, it has been proposed to use two types of certain specific hydrazone compounds in combination so as to prevent an increase in the residual potential without substantially impairing other properties of the photoreceptor (Japanese Unexamined Patent Publication No. 134767/1986). However, this proposal was not necessarily satisfactory from the viewpoint of the balance of various properties, and it has been desired to develop a technology which is capable of improving the overall properties of a photoreceptor in good balance.

It has become common to employ a semiconductor laser as a light source in the field of printers. The wavelength of the light source in this case is about 800 nm, and it is desired to develop a photoreceptor having high sensitivity to a light with a long wavelength of about 800 nm. As materials to meet this requirement, those disclosed in Japanese Unexamined Patent Publications No. 49544/1984, No. 214034/1984, No. 109056/1986, No. 171771/1986, No. 217050/1986, No. 239248/1986, No. 67094/987, No. 134651/1987, No. 275272/1987, No. 198067/1988, No. 198067/1988, No. 210942/1988 and No. 218768/1988 may be mentioned, and various oxytitanium phthalocyanines having crystal forms suitable as materials for electrophotographic photoreceptors, are known. However, an electrophotographic photoreceptor having high sensitivity to a light with a long wavelength and being excellent in other electrical properties is still desired.

The present invention has been made to solve the above-mentioned problems. The first object of the present invention is to provide an electrophotographic photoreceptor having high sensitivity and high durability.

The second object is to provide an electrophotographic photoreceptor which has high sensitivity and will undergo no substantial property change even in repeated use with the residual potential sufficiently low even when the film thickness is made thick and which is excellent in the durability.

The third object is to provide an electrophotographic photoreceptor having high sensitivity even to a light with a long wavelength of about 800 nm, wherein the chargeability, the dark attenuation, the residual potential, etc. are well-balanced.

The present inventors have conducted extensive researches for organic low molecular weight photoconductive compounds which satisfy these objects, and as a result, have found that certain specific arylamine compounds are suitable for this purpose. The present invention has been accomplished the basis of this discovery.

Thus, the present invention provides an electrophotographic photoreceptor comprising an electrically conductive substrate and a photosensitive layer formed thereon, wherein said photosensitive layer contains an arylamine compound of the following formula (I):

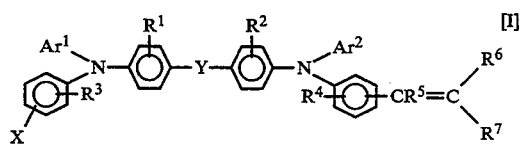

wherein X is a hydrogen atom or a group of the formula (II):

$$-CR^8 = C\diagup_{R^{10}}^{R^9} \quad \text{(II)}$$

Y is a group of the formula (III) or (IV):

$$-O-A^1-O- \quad \text{(III)}$$

$$-A^2-O-A^3- \quad \text{(IV)}$$

wherein $A^1$ in the formula (III) is a bivalent hydrocarbon residue which may have substituents, and each of $A^2$ and $A^3$ in the formula (IV) is an alkylene group which may have substituents, an arylene group which may have substituents, or a group wherein an alkylene group which may have substituents and an arylene group which may have substituents, are bonded, and $A^2$ and $A^3$ may be the same or different from each other; each of $Ar^1$ and $Ar^2$ which may be the same or different, is an alkyl group which may have substituents, an aryl group which may have substituents, or a heterocyclic group which may have substituents; each of $R^1$, $R^2$, $R^3$ and $R^4$ which may be the same or different, is a hydrogen atom, a halogen atom, an alkyl group which may have substituents, an alkoxy group which may have substituents, or a substituted amino group; each of $R^5$, $R^6$, $R^7$, $R^8$, $R^9$ and $R^{10}$ which may be the same or different, is a hydrogen atom, an alkyl group which may have substituents, an aryl group which may have substituents, or a heterocyclic group which may have substituents, or $R^6$ and $R^7$, or and $R^9 R^{10}$ are condensed to form a carbon ring group or a heterocyclic group, provided that with respect to the pair of $R^6$ and $R^7$ and the pair of $R^9$ and $R^{10}$, when one of each pair is a hydrogen atom or an alkyl group, the other is an aryl group or a heterocyclic group.

Further, the present invention provides an electrophotographic photoreceptor comprising an electrically conductive substrate and a photosensitive layer formed thereon, wherein the photosensitive layer contains the arylamine compound of the formula (I) and a pyrenehydrazone compound of the following formula (X):

$$HC=N-N\diagup_{R^{12}}^{R^{11}} \quad \text{(X)}$$

(attached to pyrene ring system)

wherein $R^{11}$ is an alkyl group, an allyl group, an aryl group which may have substituents, or an aralkyl group which may have substituents, and $R^{12}$ is an aryl group which may have substituents.

Furthermore, the present invention provides an electrophotographic photoreceptor comprising an electrically conductive substrate and a photosensitive layer formed thereon, wherein the photosensitive layer contains the arylamine compound of the formula (I) as a carrier-transporting material and an oxytitanium phthalocyanine showing a main diffraction peak at a Bragg angle ($2\theta \pm 0.2°$) of 27.3° in the X-ray diffraction spectrum, as a carrier-generating material.

Figure 1:
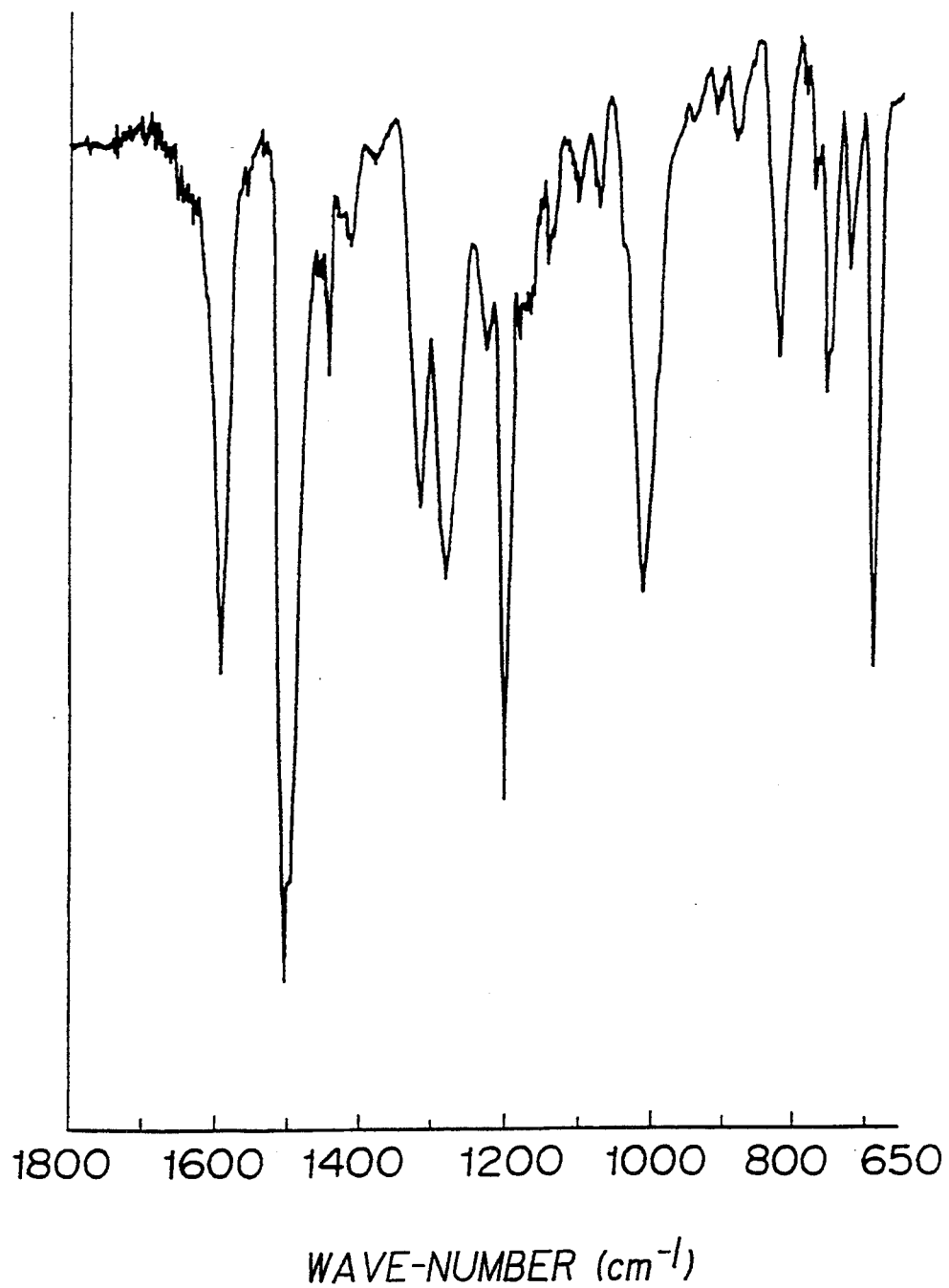
FIG. 1 shows an infrared absorption spectrum of the arylamine compound obtained in Preparation Example 2.

Now, the present invention will be described in detail.

In the electrophotographic photoreceptor of the present invention, the photosensitive layer contains an arylamine compound of the above formula (I).

In the above formula (I), X is a hydrogen atom or a group of the formula (II):

$$-CR^8 = C\diagup_{R^{10}}^{R^9} \quad \text{(II)}$$

Y is a group of the formula (III) or (IV):

$$-O-A^1-O- \quad \text{(III)}$$

$$-A^2-O-A^3- \quad \text{(IV)}$$

In the formula (III), $A^1$ is a bivalent hydrocarbon residue, for example, an alkylene group such as a methylene group, an ethylene group or a propylene group; an arylene group such as a phenylene group, a biphenylene group or a naphthylene group; a group wherein an alkylene group and a arylene group are bonded, such as xylylene group; a cycloalkylene group such as cyclohexylene group; or a vinylene group. Particularly preferred is an alkylene group, an arylene group, or a group wherein an alkylene group and an arylene group are bonded. In the formula (IV), each of $A^2$ and $A^3$ is an alkylene group, an arylene group or a group wherein an alkylene group and an arylene group are bonded, and $A^2$ and $A^3$ may be the same or different from each other Such groups of $A^1$, $A^2$ and $A^3$ may, respectively, have substituents such as a halogen atom, a hydroxyl group, a saturated or unsaturated hydrocarbon group (such as an alkyl group or an aryl group), an alkoxy group, an aryloxy group, a dialkylamino group and a diarylamino group.

Each of $Ar^1$ and $Ar^2$ which may be the same or different, is an alkyl group such as a methyl group, an ethyl group or a propyl group; an aryl group such as a phenyl group, a naphthyl group or an anthracenyl group; or a heterocyclic group such as a pyrrolyl group, a thiophenyl group, a furyl group or a carbazolyl group, preferably an aryl group or an aromatic heterocyclic group, particularly preferably a phenyl group. Such alkyl, aryl and heterocyclic groups may, respectively, have substituents. Such substituents may, for example, be a hydroxyl group; a halogen atom such as a chlorine atom, a bromine atom or an iodine atom; an alkyl group such as a methyl group, an ethyl group, a propyl group, a butyl group or a hexyl group; an alkoxy group such as a methoxy group, an ethoxy group or a butoxy group; an allyl group; an aralkyl group such as a benzyl group, a naphthylmethyl group or a phenethyl group; an aryloxy group such as a phenoxy group or a tolyloxy group; an arylalkoxy group such as a benzyloxy group or a phenethyloxy group; an aryl group such as a phenyl group or a naphthyl group; an arylvinyl group such as a styryl group or a naphthylvinyl group; dialkylamino group such as a dimethylamino group or a diethylamino group; a diarylamino group such as a diphenylamino group or a dinaphthylamino group; a diaralkylamino group such as a dibenzylamino group or a diphenethylamino group; a di-heterocyclic amino group such as a dipyridylamino group or a dithienylamino group; a diallylamino group, or a di-substituted amino group having an optional combination of the above-mentioned substituents for the amino groups.

Each of $R^1$, $R^2$, $R^3$ and $R^4$ which may be the same or different, is a hydrogen atom; a halogen atom such as a chlorine atom, a bromine atom or an iodine atom; an alkyl group such as a methyl group, an ethyl group or a propyl group; an alkoxy group such as a methoxy group, an ethoxy group or a propyloxy group; a dialkylamino group such as a dimethylamino group; a diarylamino group such as a diphenylamino group; a diaralkylamino group such as a dibenzylamino group; a di-heterocyclic amino group such as a dipyridylamino group; a diallylamino group; or a substituted amino group such as a di-substituted amino group having an optional combination of the above-mentioned substituents for the amino groups. Particularly preferred is a hydrogen atom, a methyl group or a methoxy group. The alkyl group and the alkoxy group may, respectively, have substituents. Such substituents may, for example, be a hydroxyl group; a halogen atom such as a chlorine atom, a bromine atom or an iodine atom; an alkyl group such as a methyl group, an ethyl group, a propyl group, a butyl group or a hexyl group; an alkoxy group such as a methoxy group, an ethoxy group or a butoxy group; an allyl group; an aralkyl group such as a naphthylmethyl group or a phenethyl group; an aryloxy group such as a phenoxy group or a tolyloxy group; an arylalkoxy group such as a benzyloxy group or a phenethyloxy group; an aryl group such as a phenyl group or a naphthyl group; an arylvinyl group such as a styryl group or a naphthylvinyl group; a dialkylamino group such as a dithiethylamino group or a diethylamino group; a diarylamino group such as a diphenylamino group or a dinaphthylamino group; a diaralkylamino group such as a dibenzylamino group or a diphenethylamino group; a diheterocyclic amino group such as a dipyridylamino group or a dithienylamino group; a diallylamino group; or a di-substituted amino group having an optional combination of the above-mentioned substituents for the amino groups.

Each of $R^5$, $R^6$, $R^7$, $R^8$, $R^9$ and $R^{10}$ which may be the same or different, is a hydrogen atom; an alkyl group such as a methyl group, an ethyl group or a propyl group; an aryl group such as a phenyl group, a naphthyl group or an anthracenyl group; or a heterocyclic group such as a pyrrolyl group, a thiophenyl group, a furyl group or a carbazolyl group. The heterocyclic group is preferably an aromatic heterocyclic group. The alkyl group, the aryl group and the heterocyclic group may, respectively, have substituents. Such substituents may, for example, be a hydroxyl group; a halogen atom such as a chlorine atom, a bromine atom or an iodine atom; an alkyl group such as a methyl group, an ethyl group, a propyl group, a butyl group or a hexyl group; an alkoxy group such as a methoxy group, an ethoxy group or a butoxy group; an allyl group; an aralkyl group such as a benzyl group, a naphthylmethyl group or a phenethyl group; an aryloxy group such as a phenoxy group or a tolyloxy group; an arylalkoxy group such as a benzyloxy group or a phenethyloxy group; an aryl group such as a phenyl group or a naphthyl group; an arylvinyl group such as a styryl group or a naphthylvinyl group; a dialkylamino group such as a dimethylamino group or a diethylamino group; a diarylamino group such as a diphenylamino group or a dinaphthylamino group; a diaralkylamino group such as a dibenzylamino group or a diphenethylamino group; a diheterocyclic amino group such as a dipyridyl amino group or a dithienylamino group; a diallylamino group; or a di-substituted amino group having an optional combination of the above-mentioned substituents for the amino groups.

Further, $R^6$ and $R^7$, or $R^9$ and $R^{10}$, may be condensed to form a single bond; a carbon ring group with a methylene group, an ethylene group, a carbonyl group, a vinylidene group or an ethylenylene group; or a heterocyclic group containing an oxygen atom, a sulfur atom or a nitrogen atom. Further, such rings may, respectively, have substituents. Such substituents may, for example, be an alkyl group such as a methyl group, an ethyl group or a propyl group; an aryl group such as a phenyl group, a naphthyl group or an anthracenyl group; a cyano group; an alkoxycarbonyl group; an aryloxycarbonyl group; a nitro group; or a halogen atom such as a chlorine atom, a bromine atom or an iodine atom.

However, with respect to the pair of $R^6$ and $R^7$ and the pair of $R^9$ and $R^{10}$, when one of each pair is a hydrogen atom or an alkyl group, the other is an aryl group or a heterocyclic group.

When Y in the above formula (I) is a group of the above formula (III), each of $R^5$, $R^6$, $R^7$, $R^8$, $R^9$ and $R^{10}$ which may be the same or different, is a hydrogen atom, an alkyl group which may have substituents, an aryl group which may have substituents, or a heterocyclic group which may have substituents, provided that with respect to the pair of $R^6$ and $R^7$ and the pair of $R^9$ and $R^{10}$, when one of each pair is a hydrogen atom or an alkyl group, the other is an aryl group or a heterocyclic group, or $R^6$ and $R^7$, or $R^9$ and $R^{10}$, may be condensed as shown by a dotted line in the following formula (I') or (II') to form a carbon ring group or a heterocyclic group, and such a ring may have substituents; whereby it is preferred that (1) when X is a hydrogen atom, $R^6$ and $R^7$ are condensed to form the carbon ring group or the heterocyclic group, and (2) when X is a group of the formula (II), at least one of the pairs of $R^6$ and $R^7$, and $R^9$ and $R^{10}$, are condensed to form the carbon ring group or the heterocyclic group:

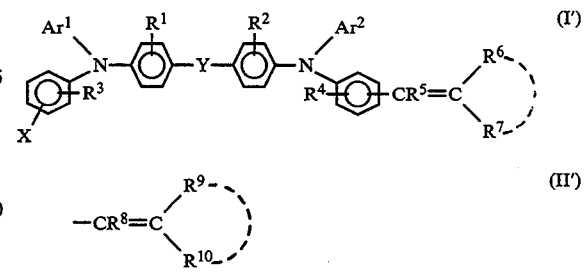

Now, typical examples of the arylamine compound of the formula (I) will be given. However, it should be understood that the arylamine compound useful in the present invention is by no means restricted to such specific examples.

A-1.
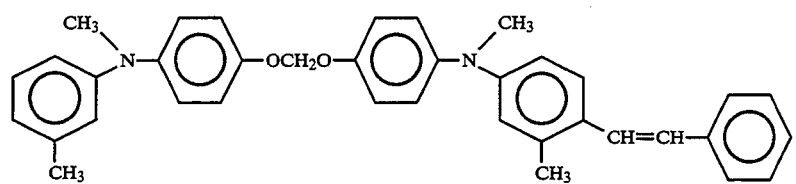
A-2.
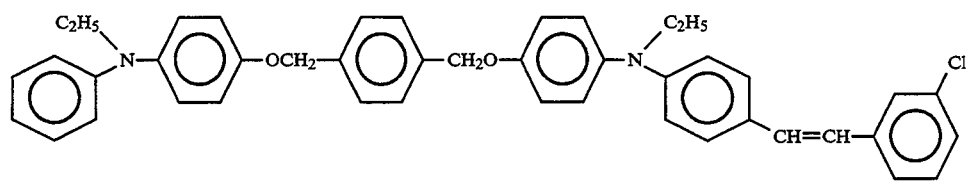
A-3.
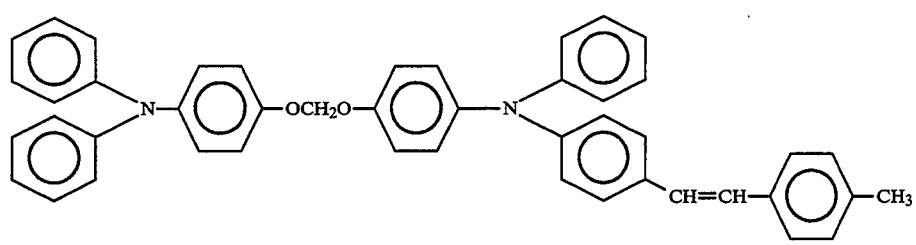
A-4.
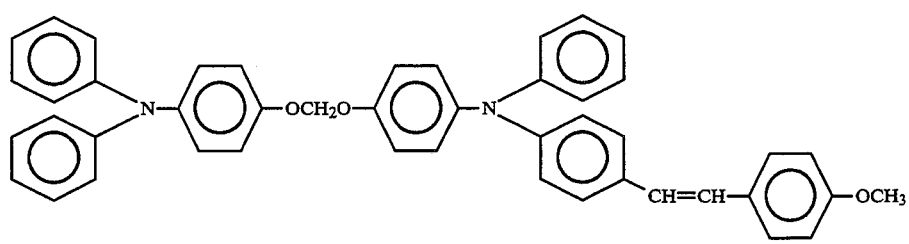
A-5.
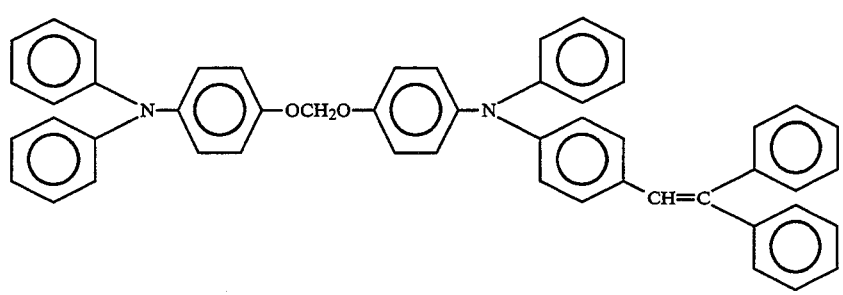
A-6.
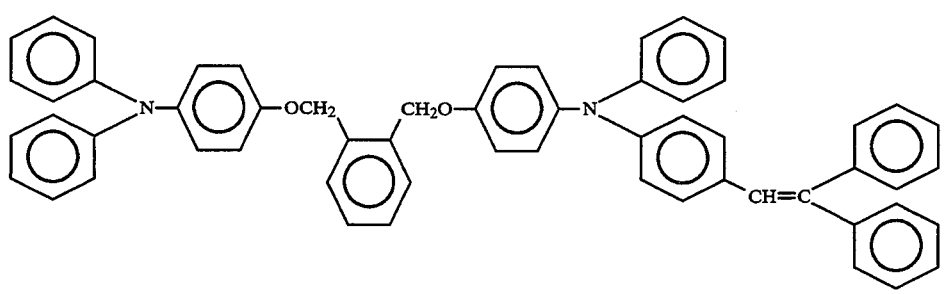
A-7.

-continued
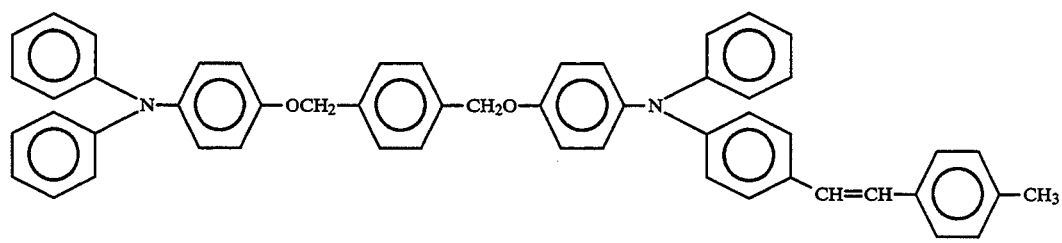
A-8.
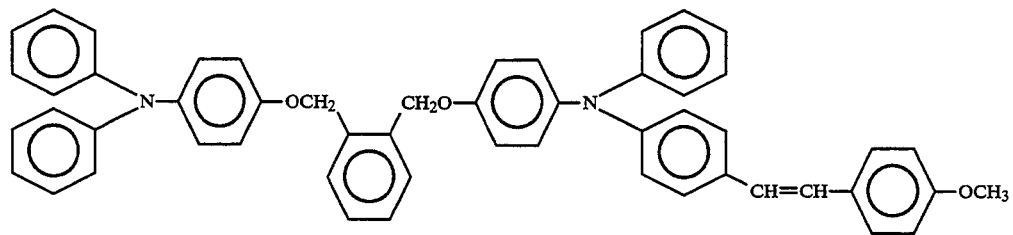
A-9.
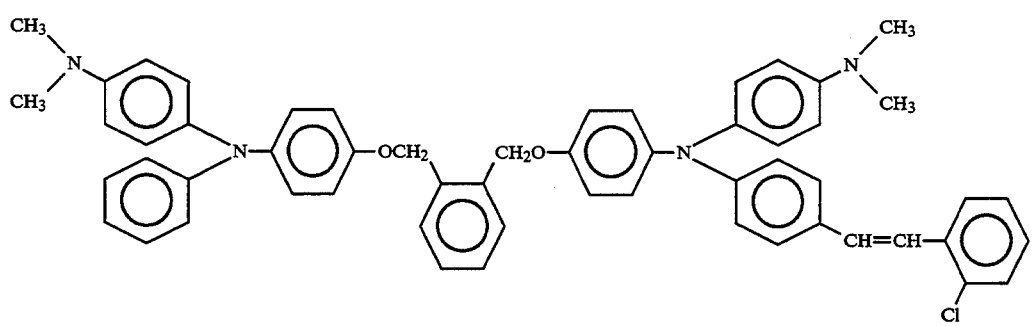
A-10.
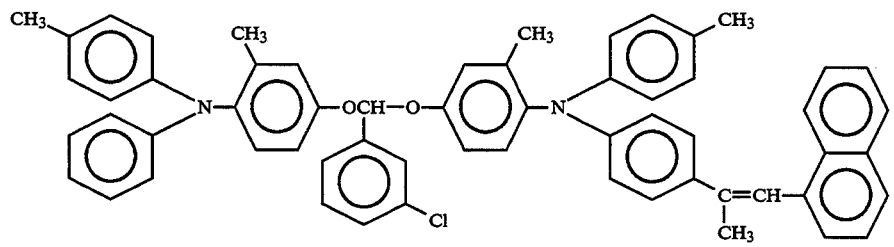
A-11.
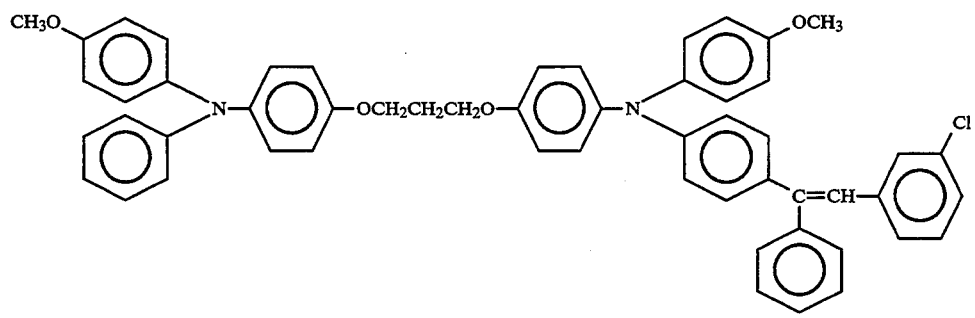
A-12.

-continued
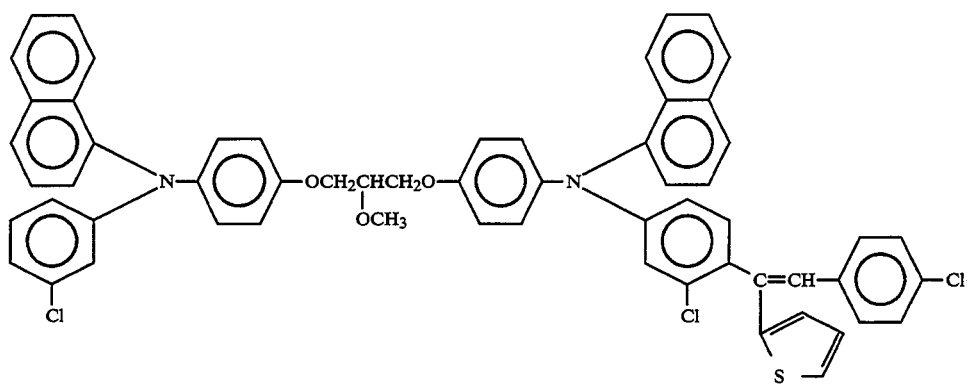
A-13.
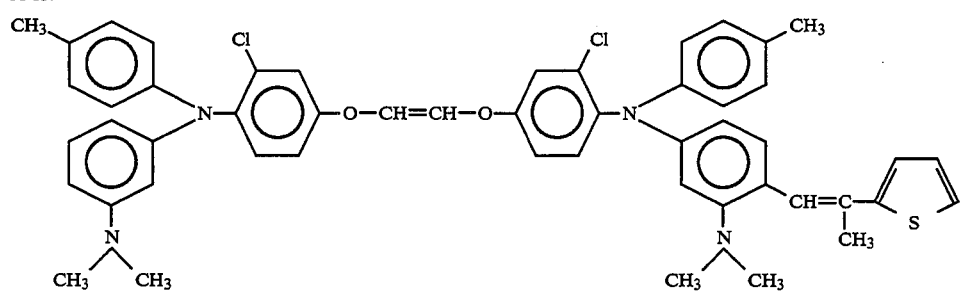
A-14.
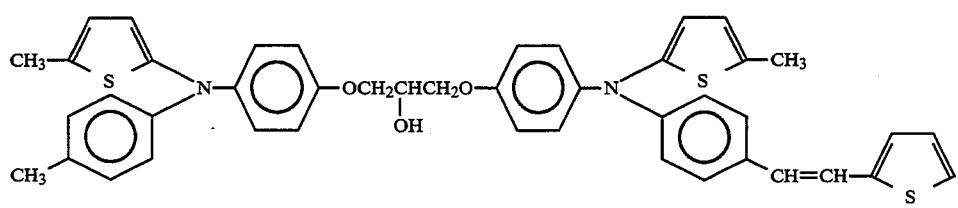
A-15.
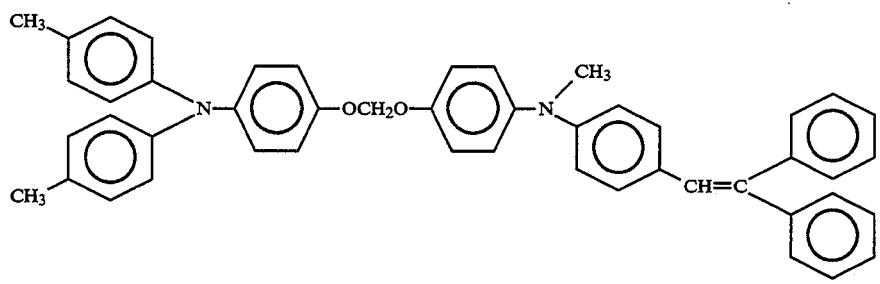
A-16.
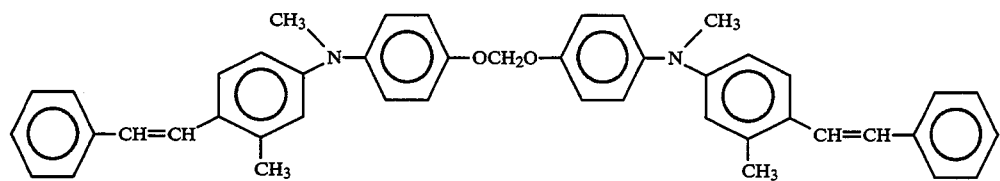
A-17.
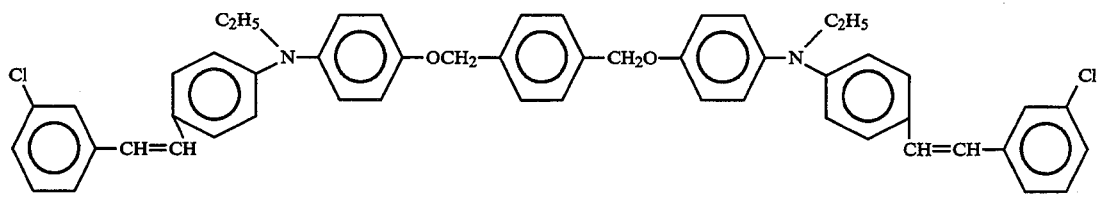

A-18.
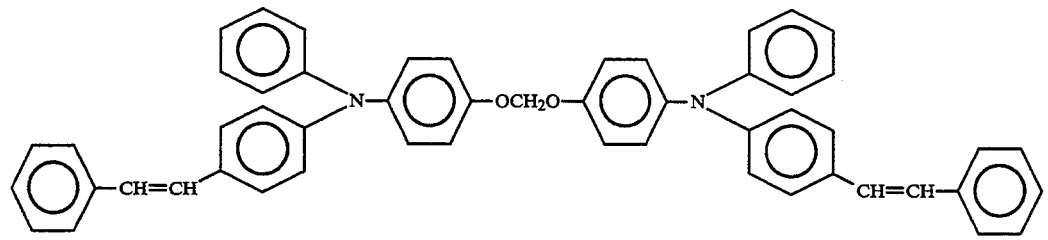
A-19.
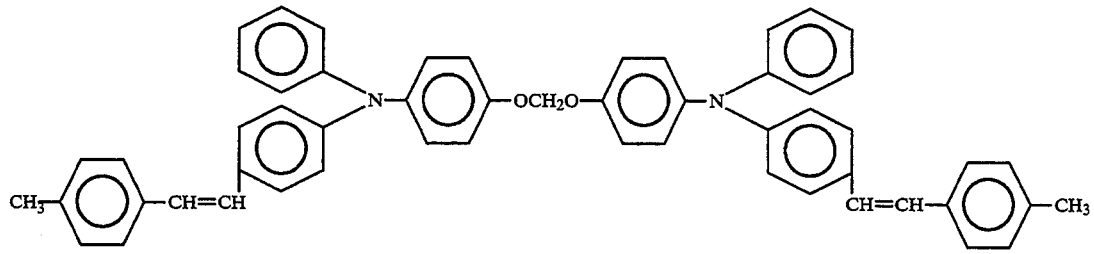
A-20.
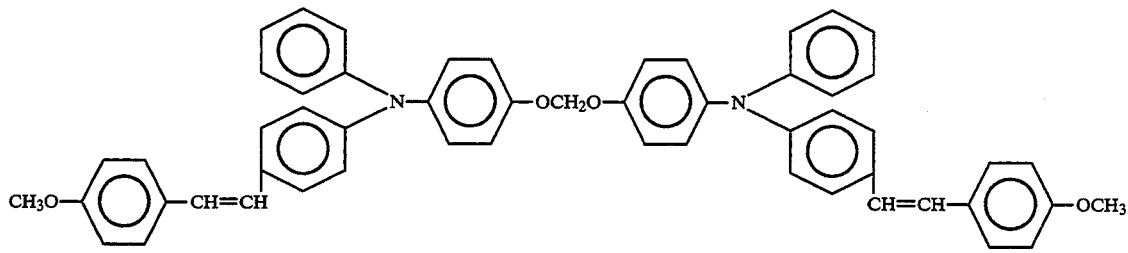
A-21.
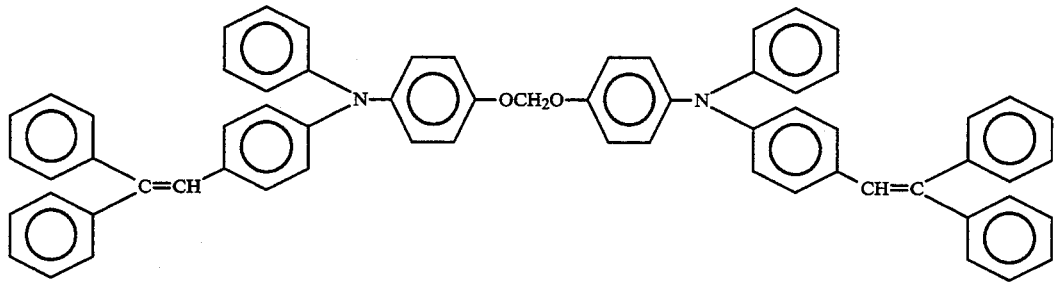
A-22: A compound corresponding to Compound 18 wherein the Y moiety is —O—CH$_2$—C$_6$H$_4$—CH$_2$—O—
A-23: A compound corresponding to Compound 19 wherein the Y moiety is —O—CH$_2$—C$_6$H$_4$—CH$_2$—O—
A-24: A compound corresponding to Compound 20 wherein the Y moiety is —O—CH$_2$—C$_6$H$_4$—CH$_2$—O—
A-25: A compound corresponding to Compound 21 wherein the Y moiety is —O—CH$_2$—C$_6$H$_4$—CH$_2$—O—

-continued

A-26: A compound corresponding to Compound 18 wherein the Y moiety is 

A-27: A compound corresponding to Compound 19 wherein the Y moiety is 

A-28: A compound corresponding to Compound 20 wherein the Y moiety is 

A-29: A compound corresponding to Compound 21 wherein the Y moiety is 

A-30: A compound corresponding to Compound 18 wherein the Y moiety is 

A-31: A compound corresponding to Compound 19 wherein the Y moiety is 

A-32: A compound corresponding to Compound 20 wherein the Y moiety is 

A-33: A compound corresponding to Compound 21 wherein the Y moiety is 

A-34,
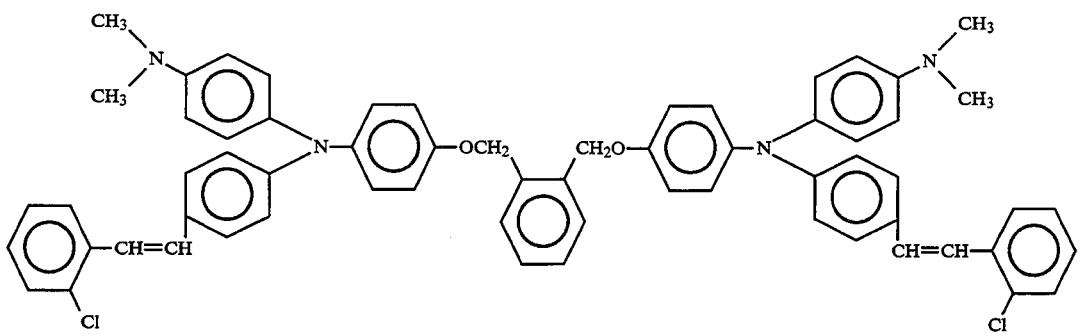

A-35.

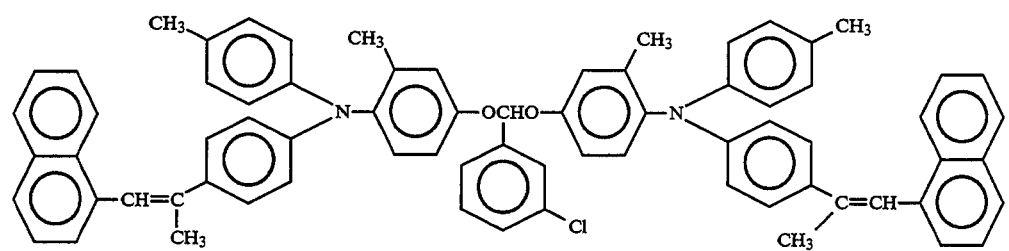
A-36.
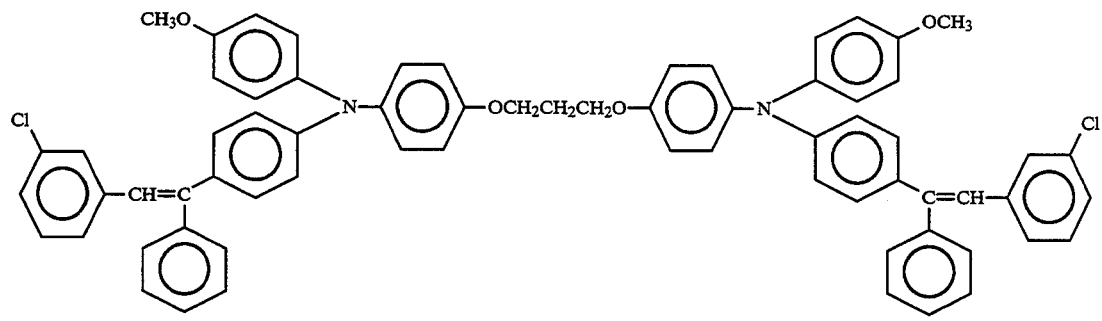
A-37.
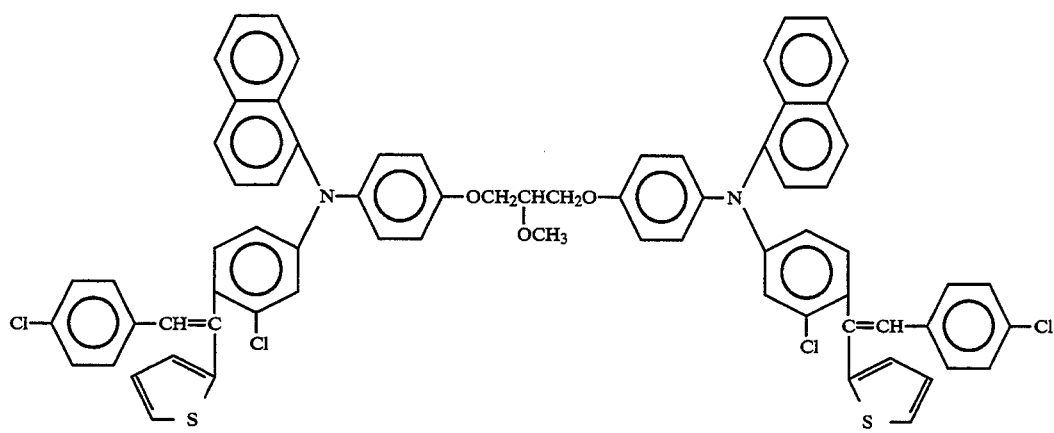
A-38.
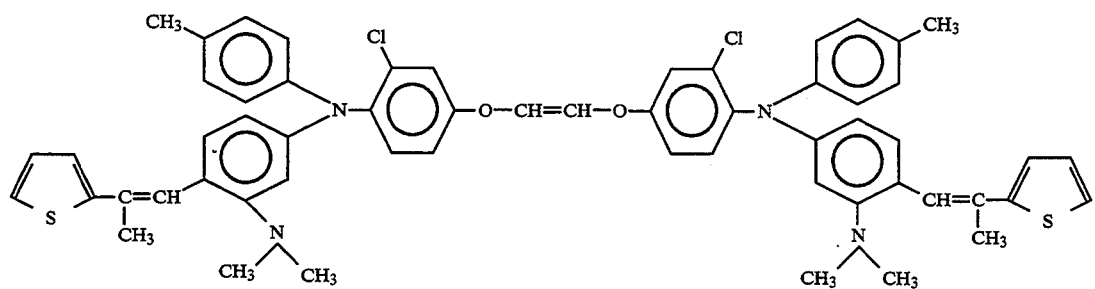
A-39.
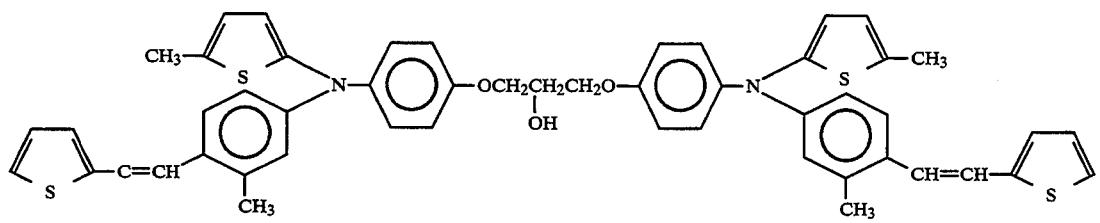
A-40.

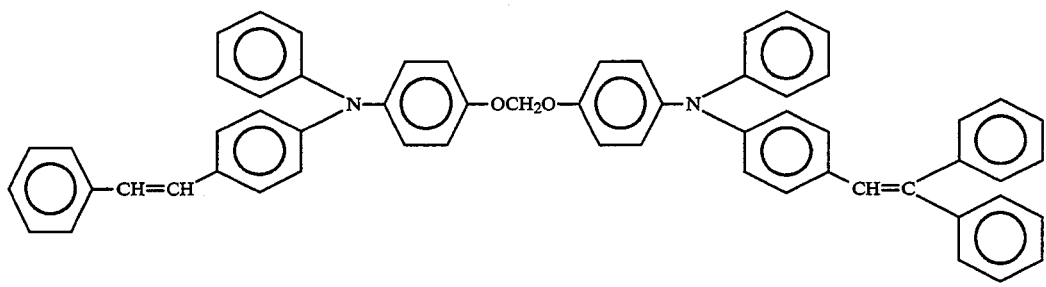
A-41.
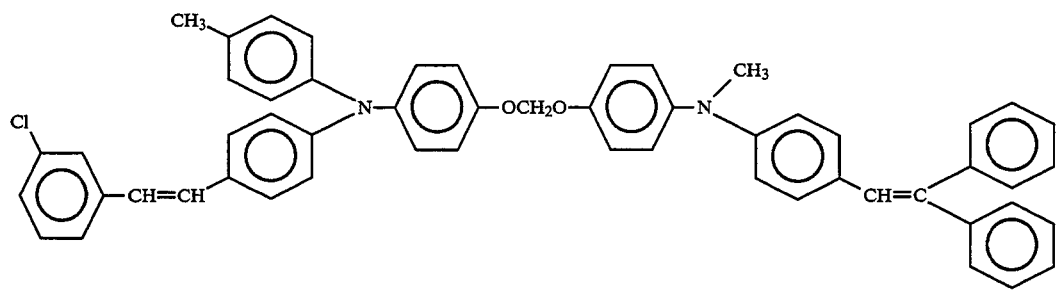
A-42.
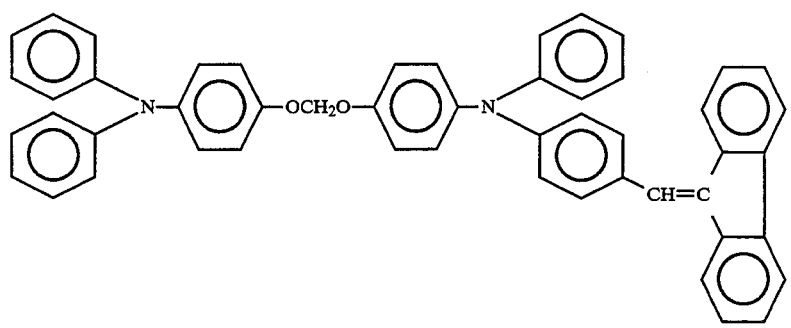
A-43.
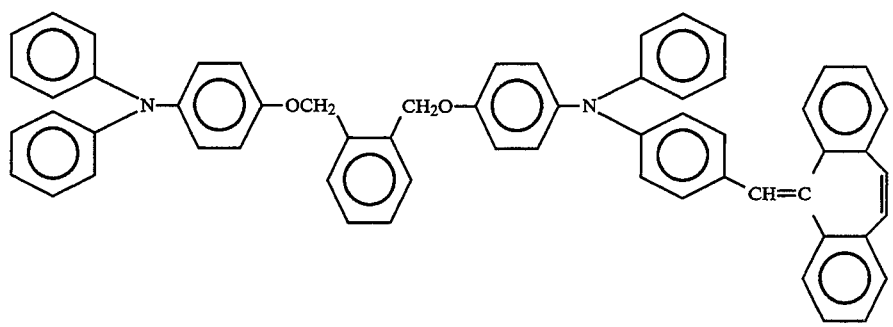
A-44.
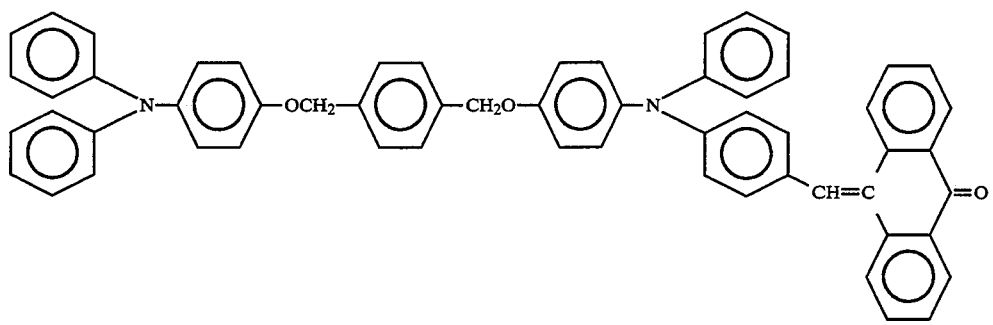

A-45.
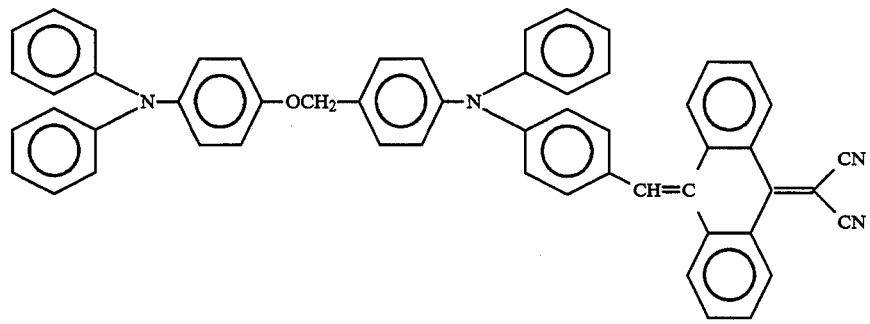
A-46.
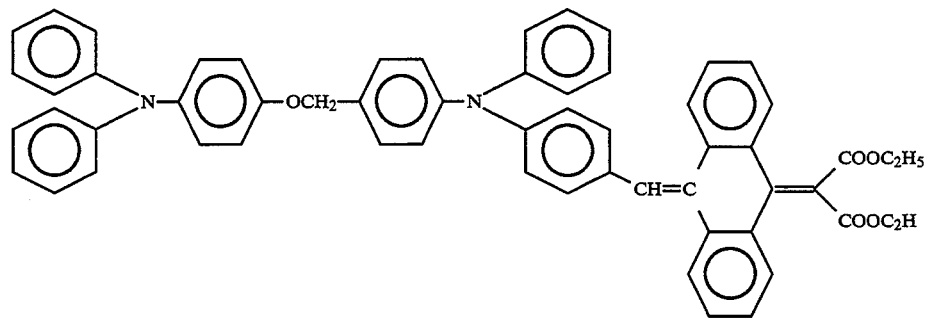
A-47.
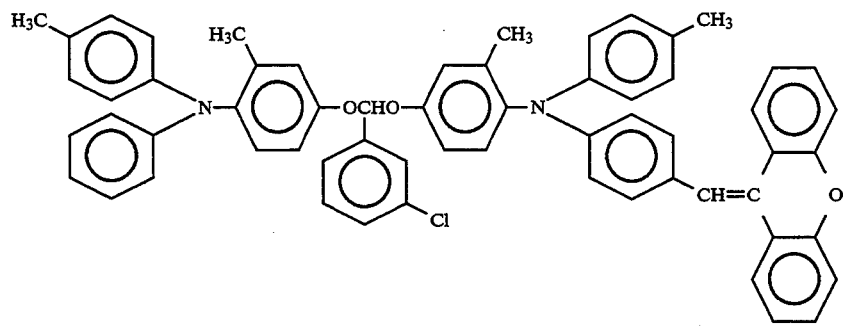
A-48.
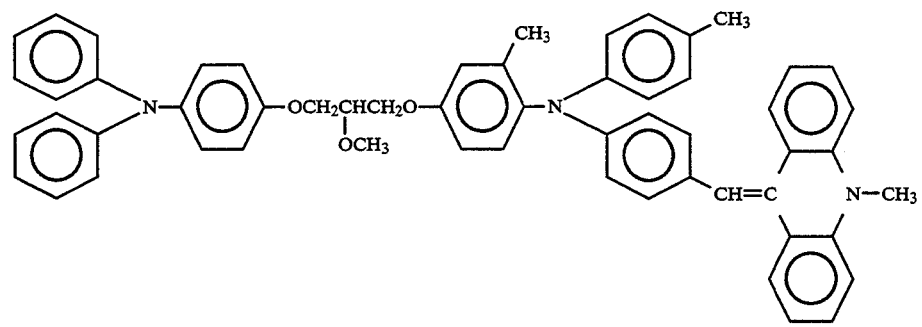
A-49.

-continued
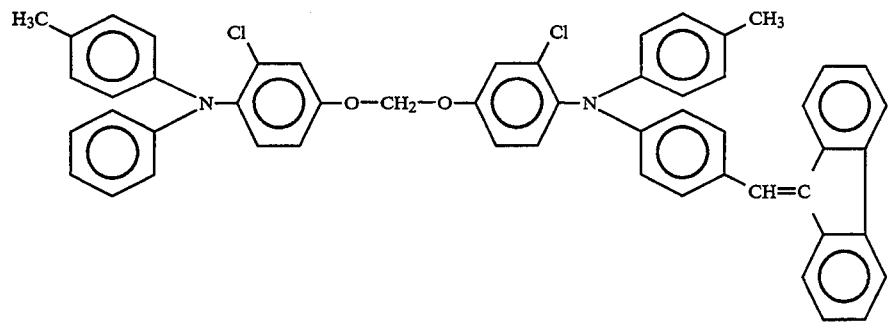
A-50.
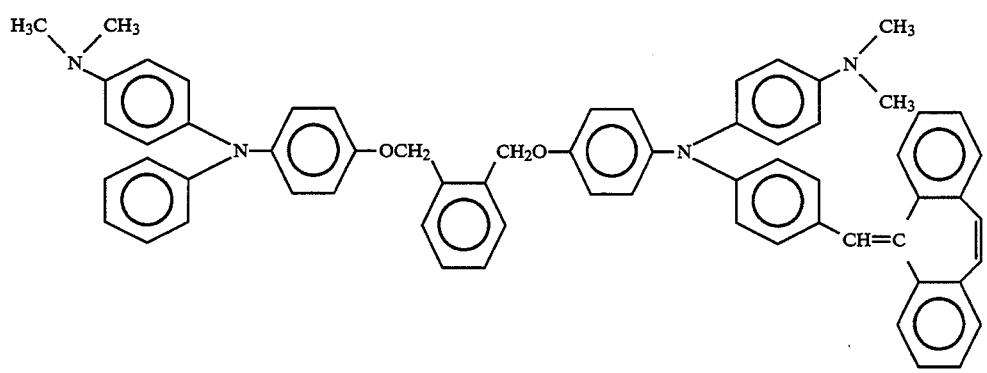
A-51.
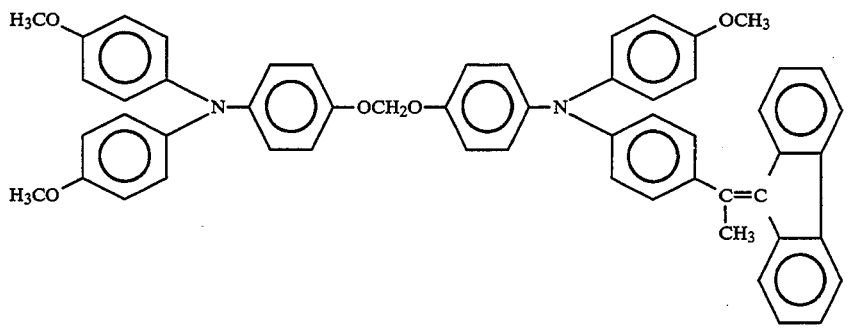
A-52.
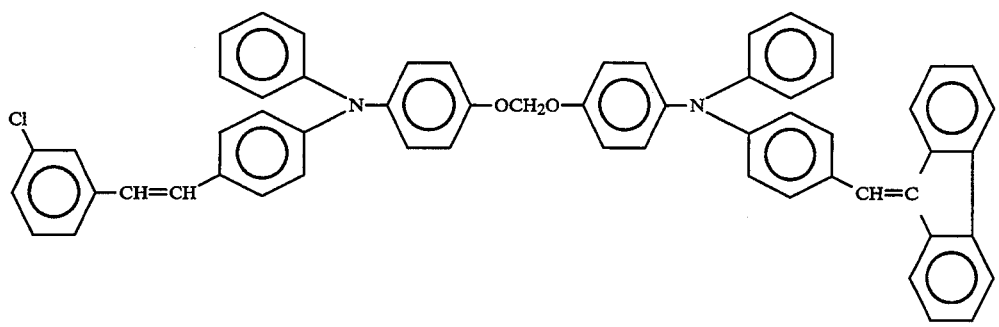
A-53.

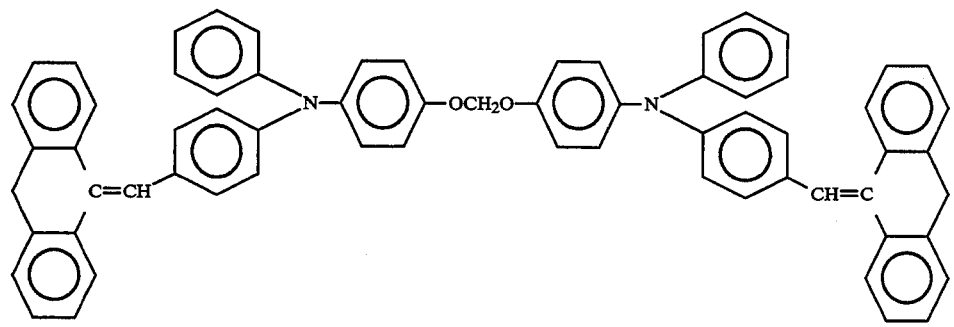
A-54.
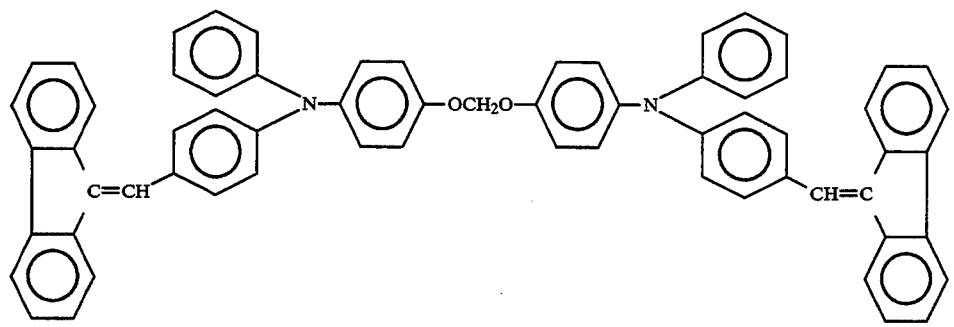
A-55.
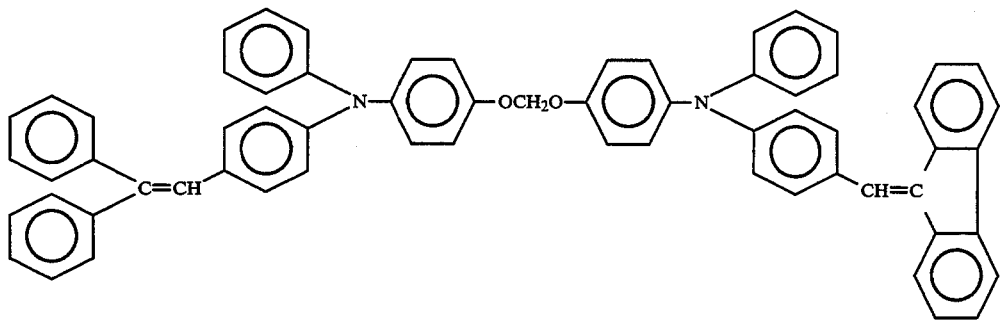
A-56.
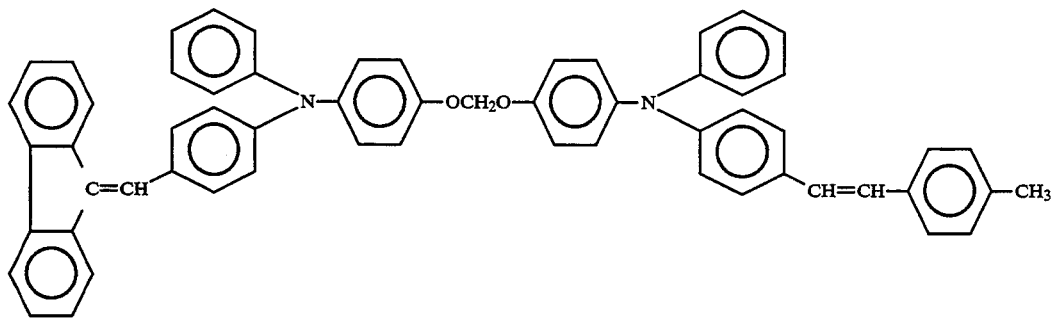
A-57.

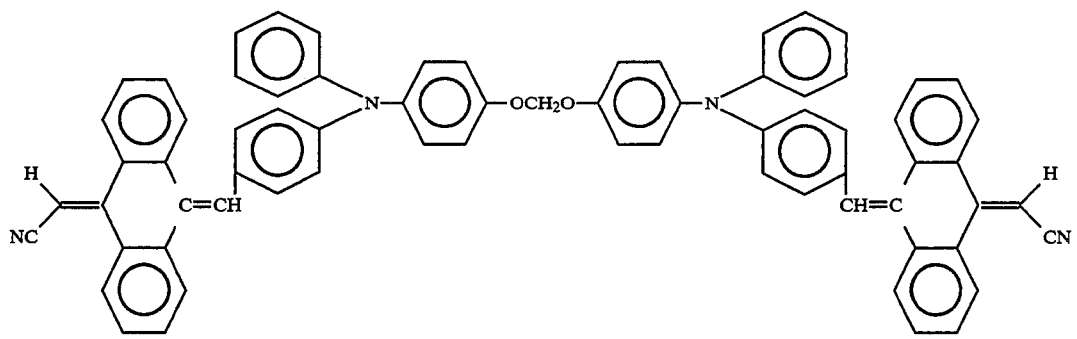
A-58.
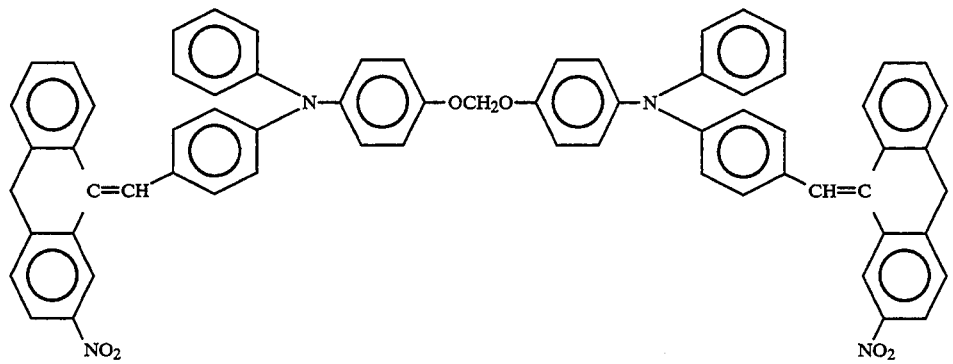
A-59.
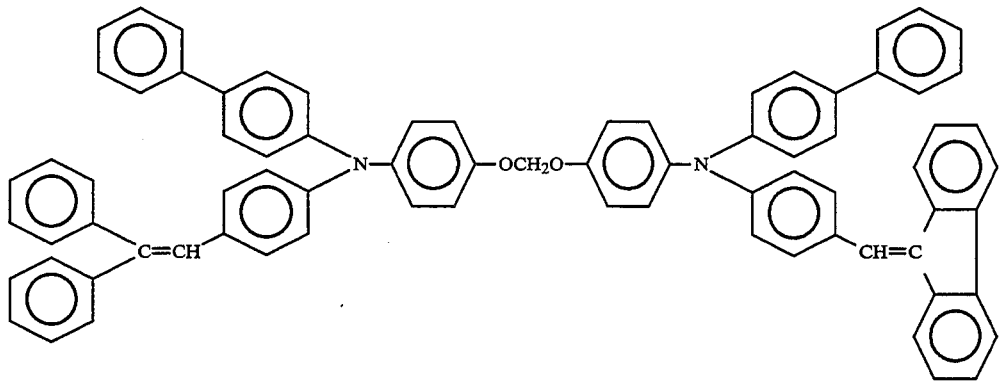
A-60: A compound corresponding to Compound 42 wherein the Y moiety is —OCH₂ 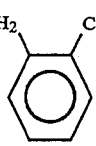 CH₂O—
A-61: A compound corresponding to Compound 52 wherein the Y moiety is —OCH₂ 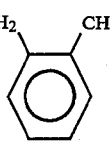 CH₂O—
A-62: A compound corresponding to Compound 53 wherein the Y moiety is —OCH₂ 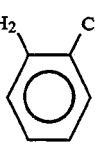 CH₂O—

-continued
A-63: A compound corresponding to Compound 54 wherein the Y moiety is 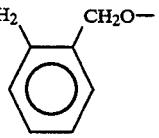
A-64: A compound corresponding to Compound 55 wherein the Y moiety is 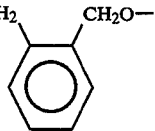
A-65: A compound corresponding to Compound 56 wherein the Y moiety is 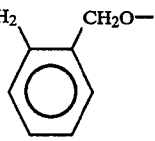
A-66.
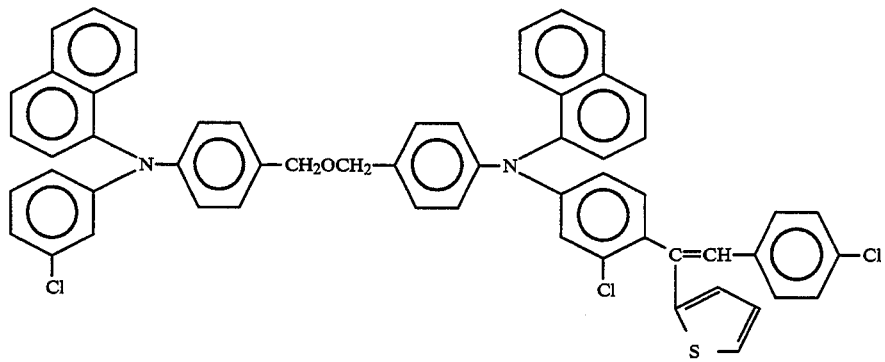
A-67.
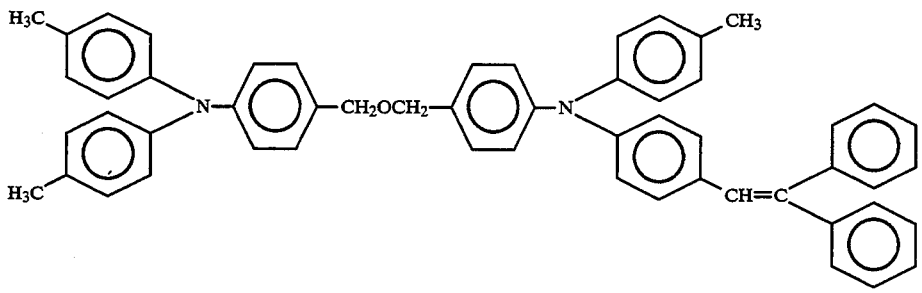
A-68.
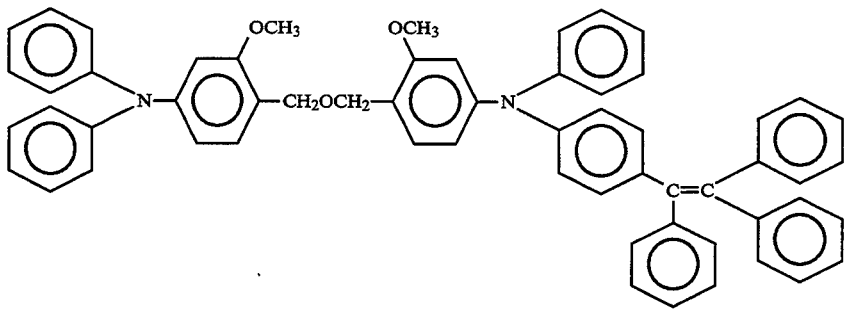
A-69.

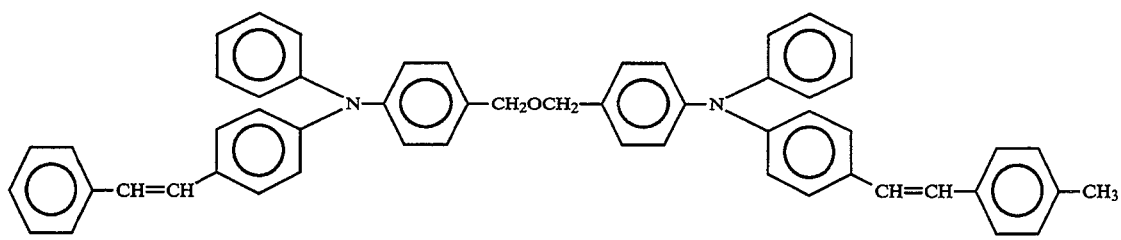
A-70.
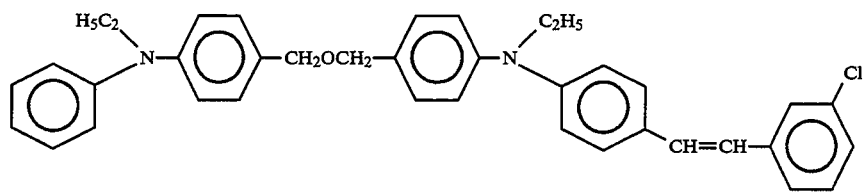
A-71.
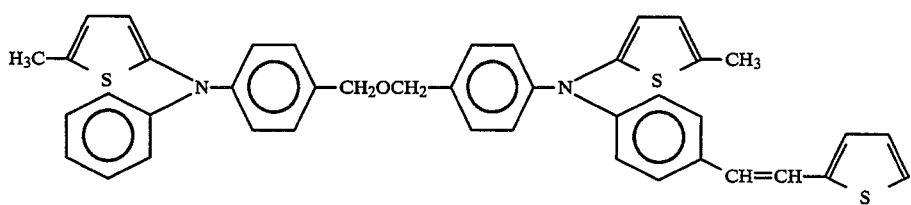
A-72
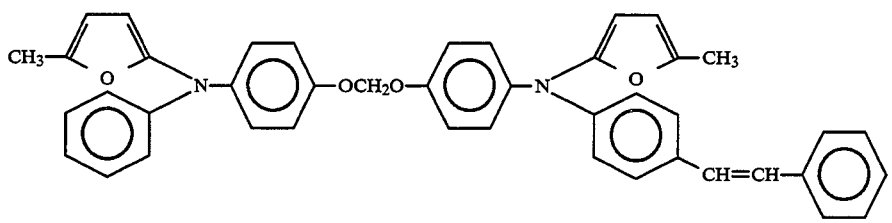
A-73
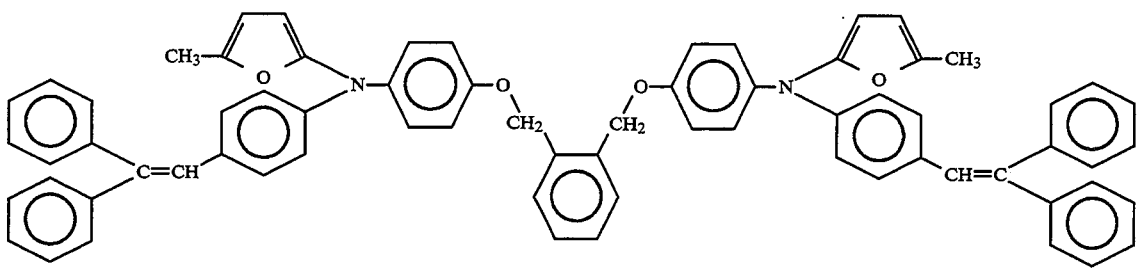
A-74
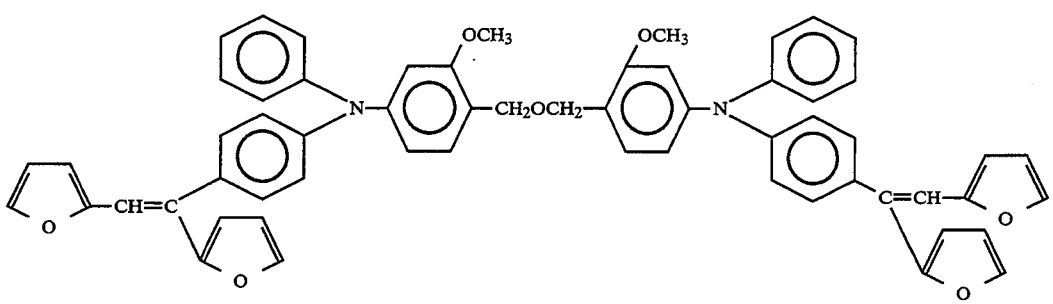
A-75

-continued

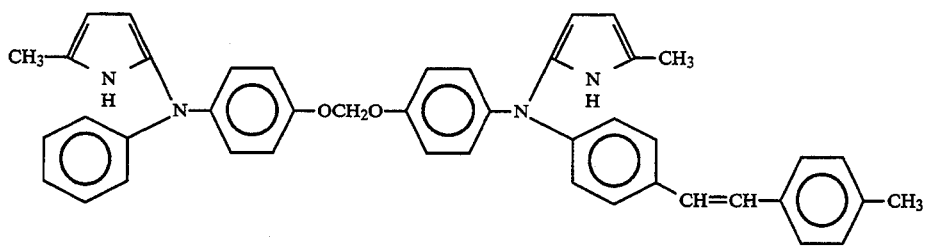

A-76

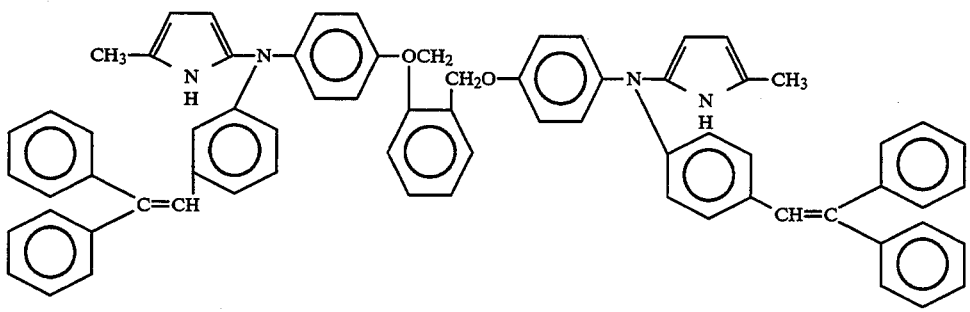

A-77

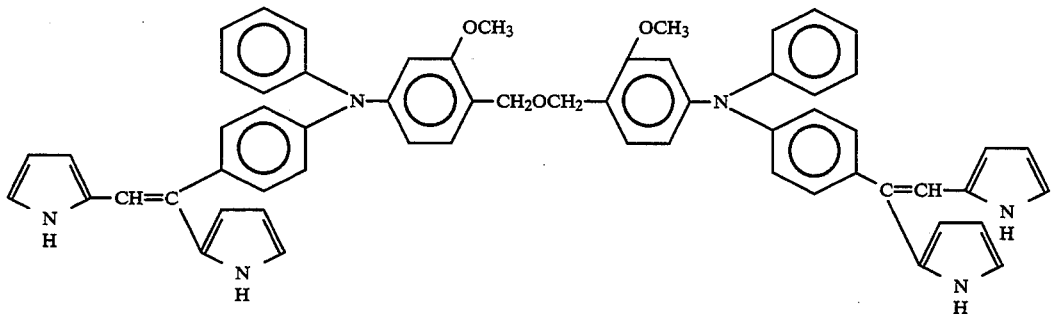

The arylamine compound of the above formula (I) can be prepared by a conventional method. A preferred method will be described with respect to cases where —X is —H, and —X is —CR$^8$=C(R$^9$)R$^{10}$ of the formula (II).

(1) When —X is —H

For example, using a known arylamine compound as the starting arterial, a conventional carbonyl-introducing reaction is conducted, followed by a Wittig reaction to obtain the desired compound.

This method will be described in further detail as follows:

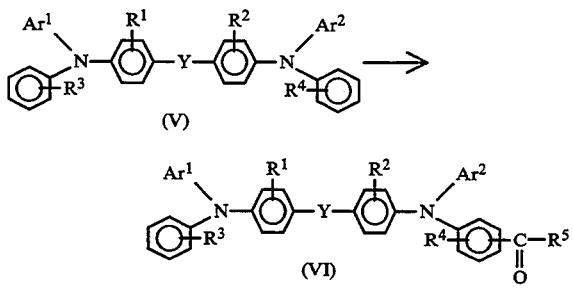

① When R$^5$=H
The arylamine compound of the formula (V) (in the formulas (V) and (VI), Ar$^1$, Ar$^2$, R$^1$, R$^2$, R$^3$, R$^4$ and R$^5$ are as defined with respect to the formula (I)) is reacted with a formylating agent such as N,N-dimethylformamide or N-methylformanilide in the presence of phosphorus oxychloride to obtain an aldehyde product of the formula (VI).

The formylating agent may be used in a large excess so that it serves as a solvent for the reaction. However, a solvent inert to the reaction such as o-dichlorobenzene or benzene may be employed.

② When R$^5$≠H
The arylamine compound of the formula (V) is reacted with an acid chloride of the formula Cl—CO—R$^5$ in a solvent such as nitrobenzene, dichloromethane or carbon tetrachloride in the presence of a Lewis acid such as aluminum chloride, iron chloride or zinc chloride to obtain a ketone product of the formula (VI).

Then, the aldehyde or ketone of the formula (VI) and a Wittig reagent obtained by reacting a halide of the formula (VII) (in the formula (VII), R$^6$ and R$^7$ are as defined with respect to the formula (I), and Q is a halogen atom such as a chlorine atom or a bromine atom) with triphenylphosphine in a known organic solvent inert to the reaction such as N,N-dimethylformamide, N,N-dimethylacetamide, tetrahydrofuran, dioxane, benzene or toluene or by reacting such a halide with a trialkoxyphosphorus compound of the formula (R$^{11}$O)$_3$P wherein R$^{11}$ is an alkyl group such as a methyl group or an ethyl group, are reacted at a temperature of from 10° to 200° C., preferably from 20° to 100° C., in the presence of a known basic catalyst such as butyl lithium, phenyl lithium, sodium methoxide, sodium ethoxide or potassium t-butoxide, to obtain a compound of the formula (I).

Here, a product of cis-form, trans-form or a mixture of cis- and trans-forms may be obtained. (Hereinafter, the formula (I) represents any one of the cis-form, the trans-form and the mixture of the cis- and trans-forms).

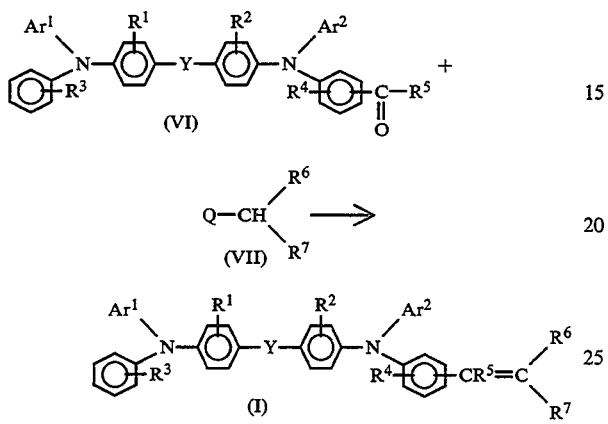

(2) When —X is

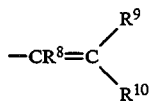

For example, using a known arylamine compound as the starting material, a conventional carbonyl-introducing reaction is conducted, followed by a Wittig reaction to obtain the desired compound.

This method will be described in detail, as follows:

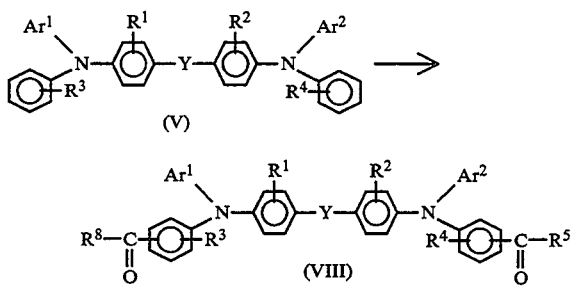

① When $R^5=R^8=H$

The arylamine compound of the formula (V) is reacted with a formylating agent such as N,N-dimethylformamide or N-methylformanilide in the presence of phosphorus oxychloride to obtain an aldehyde product of the formula (VIII) wherein $Ar^1$, $Ar^2$, $R^1$, $R^2$, $R^3$, $R^4$, $R^5$ and $R^8$ are as defined with respect to the formula (I).

The formylating agent may be used in a large excess, so that it serves as a solvent for the reaction. However, a solvent inert to the reaction, such as o-dichlorobenzene or benzene, may be employed.

② When $R^5 \neq H$, and $R^8 \neq H$

The arylamine compound of the formula (V) is reacted with an acid chloride of the formula Cl—CO—$R^5$ or Cl—CO—$R^8$ in a solvent such as nitrobenzene, dichloromethane or carbon tetrachloride in the presence of a Lewis acid such as aluminum chloride, iron chloride or zinc chloride to obtain a ketone product of the formula (VIII).

Further, $R^5$ and $R^8$ may be the same or different from each other, and when $R^5 \neq R^8$, the acid chloride to be added, may be mixed or stepwise added to accomplish the reaction.

③ When one of $R^5$ and $R^8$ is a hydrogen atom, and the other is not a hydrogen atom This can be accomplished by conducting the above two methods stepwise.

Then, the obtained aldehyde or ketone of the formula (VIII) and a Wittig reagent obtained by reacting halides of the formulas (VII) and (IX):

(in the formula (IV), $R^9$ and $R^{10}$ are as defined above with respect to the formula (I), and IX is a halogen atom such as a chlorine atom or a bromine atom), with triphenylphosphine, or by reacting such halides with a trialkoxy phosphorus compound of the formula $(R^{12}O)_3P$ (wherein $R^{12}$ is an alkyl group such as a methyl group or an ethyl group), in a known organic solvent inert to the reaction such as N,N-dimethylformamide, N,N-dimethylacetamide, tetrahydrofuran, dioxane, benzene or toluene, are reacted at a temperature of from 10° to 200° C., preferably from 20° to 100° C. in the presence of a known basic catalyst such as butyl lithium, phenyl lithium, sodium methoxide, sodium ethoxide or potassium t-butoxide, to obtain a compound of the formula (I).

Here, a product of cis-form, trans-form or a mixture of cis- and trans-forms may be obtained. (Hereinafter, the formula (I) represents any one of the cis-form, the trans-form and the mixture of the cis- and trans-forms).

The compounds of the formulas (VII) and (IX) may be used alone or in combination as a mixture. Otherwise, in some cases, they may be reacted stepwisely.

In these reactions, after completion of the respective steps or after completion of the entire process steps, the product can be purified by a conventional purification method such as recrystallization, sublimation or column chromatography to obtain a high purity product, as the case requires.

The electrophotographic photoreceptor of the present invention has a photosensitive layer containing at least one arylamine compound of the above formula (I).

The arylamine compound of the formula (I) exhibits excellent performance as an organic photoconductive material. Especially when used as a carrier transporting medium, it presents a photoreceptor having a high sensitivity and excellent durability.

Various formulations are known for photosensitive layers of electrophotographic photoreceptors. Any one of such conventional formulations may be used for the photosensitive layer of the electrophotographic photoreceptor of the present invention.

The photosensitive layer (the photoconductive layer) may be of a lamination type wherein a carrier generation layer and a carrier transport layer are laminated in this order or in a reversed order, or of a dispersion type in which particles of a carrier-generating material (a substance capable of generating electric charge carriers) are dispersed in a carrier transporting medium. For example, the photosensitive layer may be a photosensitive layer having the arylamine compound and, as the case requires, a colorant or an electron attractive compound which serves as a sensitizer, incorporated in a binder, a photosensitive layer having a carrier generating material (photoconductive particles) capable of generating electric charge carriers at an extremely high efficiency upon absorption of light and the arylamine compound incorporated in a binder, or a photosensitive layer having a carrier transport layer comprising the arylamine compound and a carrier generation layer comprising a carrier-generating material capable of generating electric charge carriers at an extremely high efficiency upon absorption of light, or such a carrier-generating material and a binder, laminated.

Such a photosensitive layer may further contain a known other arylamine compound, a hydrazone compound or a stilbene compound having excellent performance as an organic photoconductor, together with the arylamine compound of the formula (I).

In the electrophotographic photoreceptor comprising an electrically conductive substrate and a photosensitive layer formed thereon, it is preferred that the photosensitive layer contains the arylamine compound of the above formula (I) and a pyrenehydrazone compound of the following formula (X). An electrophotographic photoreceptor having two types of such specific compounds incorporated in the photosensitive layer, has a very high photosensitivity and shows a low residual potential, and it shows little accumulation of the residual potential even in repeated use. Further, the stability is excellent with little changes in the chargeability and sensitivity. Accordingly, it is excellent in durability and can be used without any problem for a high speed copying machine or printer.

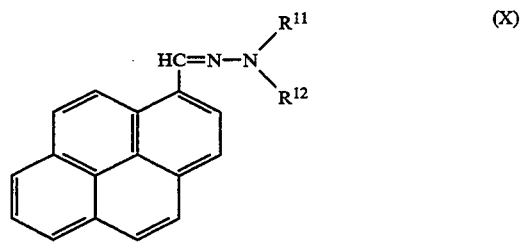

(X)

In the formula (X), $R^{11}$ is an alkyl group, an allyl group, an aryl group which may have substituents, or an aralkyl group which may have substituents, preferably an aryl group which may have substituents, more preferably a phenyl group or a naphthyl group. $R^{12}$ is an aryl group which may have substituents, preferably a phenyl group or a naphthyl group. Here, the substituents may, for example, be an alkyl group, an allyl group, an alkoxy group, an aryloxy group or a dialkylamino group.

Typical examples of the pyrenehydrazone compound of the formula (X) will be given. However, it should be understood that the pyrenehydrazone compound useful for the present invention is by no means restricted to such specific examples.

B-1: 1-Pyrenecarbaldehyde methylphenyl hydrazone,
B-2: 1-Pyrenecarbaldehyde ethylphenyl hydrazone,
B-3: 1-Pyrenecarbaldehyde allylphenyl hydrazone,
B-4: 1-Pyrenecarbaldehyde diphenyl hydrazone,
B-5: 1-Pyrenecarbaldehyde benzylphenyl hydrazone,
B-6: 1-Pyrenecarbaldehyde-phenyl-1-naphthyl hydrazone,
B-7: 1-Pyrenecarbaldehyde-phenyl-2-naphthyl hydrazone,
B-8: 1-Pyrenecarbaldehyde-phenyl-4-methoxyphenyl hydrazone,
B-9: 1-Pyrenecarbaldehyde-phenylphenoxyphenyl hydrazone,
B-10: 1-Pyrenecarbaldehyde-phenyl-3-methylphenyl hydrazone,
B-11: 1-Pyrenecarbaldehyde-phenyl-4-methylphenyl hydrazone,
B-12: 1-Pyrenecarbaldehyde-phenyl-4-methoxyphenyl hydrazone,
B-13: 1-Pyrenecarbaldehyde-phenyl-4-diethylaminophenyl hydrazone,
B-14: 1-Pyrenecarbaldehyde-di(2-naphthyl) hydrazone The blend ratio of the compound of the formula (I) to the compound of the formula (X) is usually within a range of from 95:5 to 20:80, by weight. However, in order to obtain higher effects, it is preferably within a range of from 90:10 to 40:60, by weight.

Now, typical examples of preferred combinations of the arylamine compound of the formula (I) and the pyrenehydrazone compound of the formula (X) will be given. However, it should be understood that these typical examples are given merely for the purpose of exemplification, and the combination of the arylamine compound and the pyrenehydrazone compound useful for the present invention is by no means restricted to such specific examples.

|      | Arylamine compound | Pyrenehydrazone compound |
| --- | --- | --- |
| (1)  | A-18 | B-4  |
| (2)  | A-18 | B-6  |
| (3)  | A-18 | B-7  |
| (4)  | A-18 | B-8  |
| (5)  | A-18 | B-10 |
| (6)  | A-18 | B-11 |
| (7)  | A-18 | B-12 |
| (8)  | A-19 | B-4  |
| (9)  | A-19 | B-6  |
| (10) | A-19 | B-7  |
| (11) | A-19 | B-8  |
| (12) | A-19 | B-10 |
| (13) | A-19 | B-11 |
| (14) | A-19 | B-12 |
| (15) | A-20 | B-4  |
| (16) | A-20 | B-6  |
| (17) | A-20 | B-7  |
| (18) | A-20 | B-8  |
| (19) | A-20 | B-10 |
| (20) | A-20 | B-11 |
| (21) | A-20 | B-12 |
| (22) | A-21 | B-4  |
| (23) | A-21 | B-6  |
| (24) | A-21 | B-7  |
| (25) | A-21 | B-8  |
| (26) | A-21 | B-10 |
| (27) | A-21 | B-11 |
| (28) | A-21 | B-12 |
| (29) | A-22 | B-4  |
| (30) | A-22 | B-6  |
| (31) | A-22 | B-7  |
| (32) | A-22 | B-8  |
| (33) | A-22 | B-10 |

-continued

| | Arylamine compound | Pyrenehydrazone compound |
|---|---|---|
| (34) | A-22 | B-11 |
| (35) | A-22 | B-12 |
| (36) | A-23 | B-4 |
| (37) | A-23 | B-6 |
| (38) | A-23 | B-7 |
| (39) | A-23 | B-8 |
| (40) | A-23 | B-10 |
| (41) | A-23 | B-11 |
| (42) | A-23 | B-12 |
| (43) | A-24 | B-4 |
| (44) | A-24 | B-6 |
| (45) | A-24 | B-7 |
| (46) | A-24 | B-8 |
| (47) | A-24 | B-10 |
| (48) | A-24 | B-11 |
| (49) | A-24 | B-12 |
| (50) | A-25 | B-4 |
| (51) | A-25 | B-6 |
| (52) | A-25 | B-7 |
| (53) | A-25 | B-8 |
| (54) | A-25 | B-10 |
| (55) | A-25 | B-11 |
| (56) | A-25 | B-12 |
| (57) | A-26 | B-4 |
| (58) | A-26 | B-6 |
| (59) | A-26 | B-7 |
| (60) | A-26 | B-8 |
| (61) | A-26 | B-10 |
| (62) | A-26 | B-11 |
| (63) | A-26 | B-12 |
| (64) | A-27 | B-4 |
| (65) | A-27 | B-6 |
| (66) | A-27 | B-7 |
| (67) | A-27 | B-8 |
| (68) | A-27 | B-10 |
| (69) | A-27 | B-11 |
| (70) | A-27 | B-12 |
| (71) | A-28 | B-4 |
| (72) | A-28 | B-6 |
| (73) | A-28 | B-7 |
| (74) | A-28 | B-8 |
| (75) | A-28 | B-10 |
| (76) | A-28 | B-11 |
| (77) | A-28 | B-12 |
| (78) | A-29 | B-4 |
| (79) | A-29 | B-6 |
| (80) | A-29 | B-7 |
| (81) | A-29 | B-8 |
| (82) | A-29 | B-10 |
| (83) | A-29 | B-11 |
| (84) | A-29 | B-12 |
| (85) | A-30 | B-4 |
| (86) | A-30 | B-6 |
| (87) | A-30 | B-7 |
| (88) | A-30 | B-8 |
| (89) | A-30 | B-10 |
| (90) | A-30 | B-11 |
| (91) | A-30 | B-12 |
| (92) | A-31 | B-4 |
| (93) | A-31 | B-6 |
| (94) | A-31 | B-7 |
| (95) | A-31 | B-8 |
| (96) | A-31 | B-10 |
| (97) | A-31 | B-11 |
| (98) | A-31 | B-12 |
| (99) | A-32 | B-4 |
| (100) | A-32 | B-6 |
| (101) | A-32 | B-7 |
| (102) | A-32 | B-8 |
| (103) | A-32 | B-10 |
| (104) | A-32 | B-11 |
| (105) | A-32 | B-12 |
| (106) | A-33 | B-4 |
| (107) | A-33 | B-6 |
| (108) | A-33 | B-7 |
| (109) | A-33 | B-8 |
| (110) | A-33 | B-10 |
| (111) | A-33 | B-11 |
| (112) | A-33 | B-12 |
| (113) | A-40 | B-4 |
| (114) | A-40 | B-6 |
| (115) | A-40 | B-7 |
| (116) | A-40 | B-8 |
| (117) | A-40 | B-10 |
| (118) | A-40 | B-11 |
| (119) | A-40 | B-12 |

In the present invention, it is possible to obtain a photoreceptor which has a particularly high sensitivity and a low residual potential and which is excellent in the durability with no substantial change in the surface potential or no substantial deterioration of the sensitivity, or no substantial accumulation of the residual potential, in repeated use, especially when the arylamine compound of the above formula (I) is used in the carrier transport layer of the photosensitive layer comprising two layers i.e. the carrier generation layer and the carrier transport layer.

Specifically, such a photoreceptor is a lamination type photoreceptor which is usually prepared in such a manner that a carrier-generating material is directly vapor-deposited or coated in the form of a dispersion with a binder, to form a carrier generation layer, and an organic solvent solution containing the above arylamine compound is cast thereon, or the above arylamine compound is dissolved together with e.g. a binder and the resulting dispersion is coated thereon, to form a carrier transport layer containing the carrier-transporting material including the arylamine compound of the above formula (I). The order of lamination of the carrier generation layer and the carrier transport layer may be reversed.

Otherwise, it may be a single layer type photoreceptor having the carrier-generating material and the carrier-transporting material coated on an electrically conductive substrate in a state dispersed or dissolved in a binder.

The carrier-generating material may, for example, be inorganic photoconductive particles of e.g. selenium, a selenium-tellurium alloy, a sellenium-arsenic alloy, cadmium sulfide or amorphous silicon; or organic photoconductive particles of e.g. metal free phthalocyanine, metal-containing phthalocyanine, perynone pigment, thioindigo, quinacridone, perylene pigment, anthraquinone pigment, azo pigment, bisazo pigment, trisazo pigment, tetrakisazo pigment or cyanine pigment.

Further, various organic pigments and dyestuffs such as a polycyclic quinone, a pyrylium salt, a thiopyrilium salt, indigo, anthoanthrone and pyranthrone, may be used. Among them, metal-free phthalocyanine, phthalocyanine having a metal or its oxide or chloride, such as indium copper chloride, galium chloride, tin, oxytitanium, zinc or vanadium, coordinated, or an azo pigment such as a monoazo pigment, a bisazo pigment, a trisazo pigment or polyazo pigment, is preferred.

Especially when a metal-containing phthalocyanine and an arylamine compound of the above formula (I) are used in combination, it is possible to obtain a photoreceptor having an improved sensitivity to a laser beam. Particularly preferred is an electrophotographic photoreceptor having a photosensitive layer containing at least a carrier-generating material and a carrier-transporting material formed on an electrically conductive substrate, wherein an oxytitanium phthalocyanine showing a main diffraction peak at a Bragg angle $(2\theta \pm 0.2°)$ of 27.3° in the X-ray diffraction spectrum, is contained as the carrier-generating material, and the arylamine compound of the above formula (I) is contained as the carrier-transporting material.

The electrophotographic photoreceptor thus obtained, has a high sensitivity, a low residual potential and high chargeability and will undergo little change in repeated use. It is useful as a highly durable photoreceptor, since the charge stability affecting the image density, is excellent. Further, it has a high sensitivity in a wavelength region from 750 to 850 nm, and it is suitable particularly as a photoreceptor for a semiconductor laser printer.

The oxytitanium phthalocyanine to be used as the carrier-generating material, has a main diffraction peak at a Bragg angle ($2\theta \pm 0.2°$) of 27.3° in the X-ray diffraction spectrum. The "main diffraction peak" means a peak at which the intensity is highest in the X-ray diffraction spectrum.

In the powder X-ray spectrum of the oxytitanium phthalocyanine to be used, the diffraction peak at a Bragg angle ($2\theta \pm 0.2°$) of 27.3° is the main peak, and other peaks may vary depending upon delicate conditions. However, the intensity (the height of the peak) of each of such other peaks is preferably not higher than 50% of the peak intensity at 27.3° in view of the chargeability and sensitivity of the electrophotographic photoreceptor.

The method for preparing the oxytitanium phthalocyanine is not particularly limited. For example, it can be prepared by the following methods.

① A method for producing (II)-type crystals disclosed in Preparation Example 1 in Japanese Unexamined Patent Publication No. 67094/1987. Namely, orthophthalodinitrile and a titanium halide are heated and reacted in an inert organic solvent, followed by hydrolysis.

② An oxytitanium phthalocyanine of any crystal form is subjected directly to heat treatment together with sulfuric acid or a sulfonated product of the formula R—SO$_3$H (wherein R is an aliphatic or aromatic residue which may have substituents) in an organic acid solvent, and in some cases, followed by heat treatment with a solvent mixture of an insoluble organic solvent and water.

③ If desired, it is preliminarily dissolved in concentrated sulfuric acid and then discharged into ice water, or pulverized by a conventional method of mechanical pulverization using e.g. a paint shaker, a ball mill or a sand grind mill, followed by heat treatment with the above-mentioned sulfonated product or heat treatment with the solvent mixture of an water-insoluble organic solvent and water. ④ In the above treatment with the sulfonated product, a mechanical pulverization method using e.g. a paint shaker, a ball mill or a sand grind mill, is used in combination instead of the heat treatment.

The oxytitanium phthalocyanine particles showing a main diffraction peak at a Bragg angle ($2\theta \pm 0.2°$) of 27.3° in the X-ray diffraction spectrum, are dissolved or dispersed in a solvent together with a binder polymer and optional other organic photoconductive compounds, pigments, electron attractive compounds, etc., and the coating solution thereby obtained, is coated and dried to form a carrier generation layer. For example, it is preferred to use an oxytitanium phthalocyanine showing a main diffraction peak at a Bragg angle ($2\theta \pm 0.2°$) of 27.3° in the X-ray diffraction spectrum and an oxytitanium phthalocyanine showing main diffraction peaks at Bragg angles ($2\theta \pm 0.2°$) of 9.3°, 13.2°, 26.2° and 27.1° in the X-ray diffraction spectrum, or an oxytitanium phthalocyanine showing a main diffraction peak at a Bragg angle ($2\theta \pm 0.2°$) of 27.3° in the X-ray diffraction spectrum and a dichloro tin phthalocyanine showing main diffraction peaks at Bragg angles ($2\theta \pm 0.2°$) of 8.5° C., 12.2°, 13.8°, 16.9°, 22.4°, 28.4° and 30.1° in the X-ray diffraction spectrum.

The dye to be incorporated, as the case requires, in the present invention, may, for example, be a triphenylmethane dye such a Methyl Violet, Brilliant Green or Crystal Violet, a thiazine dye such as Methylene Blue, a quinone dye such as Quinizarin, or a cyanine dye as well as a pyrylium salt, a thiapyrilium salt or a benzopyrylium salt. Further, the electron attracting compound which forms a carrier-transporting complex together with the arylamine compound, may, for example, be a quinone such as chloranil, 2,3-dichloro-1,4-naphthoquinone, 1-nitroanthraquinone, 1-chloro-5-nitroanthraquinone, 2-chloroanthraquinone or phenanthrenequinone; an aldehyde such as 4-nitrobenzaldehyde; a ketone such as 9-benzoylanthracene, indanedione, 3,5-dinitrobenzophenone, 2,4,7-trinitrofluorenone, 2,4,5,7-tetranitrofluorenone or 3,3',5,5'-tetranitrobenzophenone; an acid anhydride such as phthalic anhydride or 4-chloronaphthalic anhydride; a cyano compound such as tetracyano ethylene, terephthalalmalononitrile, 9-anthrylmethylidenemalononitrile, 4-nitrobenzalmalononitrile, 4-(p-nitrobenzoyloxy)benzalmalononitrile; or a phthalide such as 3-benzalphthalide, 3-($\alpha$-cyano-p-nitrobenzal)phthalide or 3-($\alpha$-cyano-p-nitrobenzal)-4,5,6,7-tetrachlorophthalide.

The carrier generation layer in the lamination type photosensitive layer may be in the form of a dispersion layer wherein the fine particles of such a material are bound by a various binder resin such as a polyester resin, polyvinyl acetate, polyester, polycarbonate, polyvinyl acetoacetal, polyvinyl propional, polyvinyl butyral, a phenoxy resin, an epoxy resin, a urethane resin, a cellulose ester or a cellulose ether. Further, the binder resin may, for example, be a polymer or a copolymer of a vinyl compound such as styrene, vinyl acetate, vinyl chloride, an acrylic acid ester, a methacrylic acid ester, vinyl alcohol or ethyl vinyl ether, a polyamide or a silicon resin. In such a case, the proportion of the carrier-generating material (substance capable of generating electric charge carriers) is usually within a range of from 20 to 2000 parts by weight, preferably from 30 to 500 parts by weight, more preferably from 33 to 500 parts by weight, per 100 parts by weight of the binder resin. The thickness of the carrier generation layer is usually from 0.05 to 5 μm, preferably from 0.1 to 2 μm, more preferably from 0.15 to 0.8 μm. The carrier generation layer may contain a leveling agent or an antioxidant to improve the coating properties or various additives such as a sensitizer, as the case requires. Further, the carrier generation layer may be a film formed by vapor deposition of the above-mentioned carrier-generating material.

In the case of a dispersion type photosensitive layer, the particle size of the carrier-generating material is required to be sufficiently small and is preferably not larger than 1 μm, more preferably not larger than 1.5 μm. The amount of the carrier-generating material dispersed in the photosensitive layer is usually within a range of from 0.5 to 50% by weight. If the amount is too small, no adequate sensitivity will be obtained. On the other hand, if the amount is too much, there will be an adverse effect such as a deterioration in the chargeability or a deterioration in the sensitivity. More preferably, it is used within a range of from 1 to 20% by weight.

The thickness of the dispersion type photosensitive layer is usually from 5 to 50 μm, preferably from 10 to 45 μm. Also in this case, a known plasticizer to improve the film-forming properties, the flexibility or the mechanical strength, an additive to control the residual potential, a dispersion adjuvant to improve the stability of the dispersion, a leveling agent to improve the coating property, a surfactant such as silicon oil or a fluorine-type oil, or other additives, may be incorporated.

Further, the photosensitive layer of the electrophotographic photoreceptor of the present invention may contain a well-known plasticizer to improve the film-forming properties, the flexibility or the mechanical strength. As the plasticizer to be incorporated to the above coating solution for this purpose, an aromatic compound such as a phthalic acid ester, a. phosphoric acid ester, an epoxy compound, chlorinated paraffin, a chlorinated fatty acid ester or methyl naphthalene, may be mentioned. In a case where the arylamine compound is used as a carrier-transporting material in the carrier transport layer, the coating solution may be of the above composition, but the photoconductive particles, the dye and the electron attracting compound may be eliminated or may be incorporated in small amounts. In this case, the carrier generation layer may be a thin layer formed by coating and drying a coating solution obtained by dissolving or dispersing the above photoconductive particles and optionally a binder polymer as well as other organic photoconductive material, a dye and an electron attracting compound in a solvent, or a layer obtained by forming the above photoconductive particles into a film by a method such as vapor deposition.

The photoreceptor thus formed, may, of course, have a layer for improving the electrical properties or mechanical properties such as an interlayer like a barrier layer, an adhesive layer or a blocking layer, a transparent insulating layer, or a protective layer, as the case requires. As a conductive substrate on which the photosensitive layer is formed, any substrate which is commonly employed in conventional electrophotographic photoreceptors, may be employed. Specifically, a drum or sheet made of a metal material such as aluminum, stainless steel, copper or nickel, or a laminate of foils or such a metal or a vapor-deposited product of such a metal, or an insulating substrate such as a polyester film or paper having a conductive layer of e.g. aluminum, copper, palladium, tin oxide or indium oxide formed on its surface, may be mentioned. Further, a plastic film, a plastic drum, paper or a paper tube having a conductive material such as metal powder, carbon black, copper iodide or a polymer electrolyte coated together with a suitable binder for conductive treatment, may be mentioned. Furthermore, a plastic sheet or drum having a conductive material such as metal powder, carbon black or carbon fiber incorporated to have electrical conductivity, may be mentioned. Still further, a plastic film or belt treated for electrical conductivity with a conductive metal oxide such as tin oxide or indium oxide, may be mentioned.

Among them, an endless type of a metal such as aluminum, is a preferred substrate.

As the barrier layer or the interlayer, an anodized aluminum film, an inorganic layer such as aluminum oxide or aluminum hydroxide, or an organic layer such as polyvinyl alcohol, casein, polyvinyl pyrrolidone, polyacrylic acid, a cellulose, gelatin, starch, polyurethane, polyimide or polyamide, may be used.

The electrophotographic photoreceptor of the present invention can be prepared by a conventional method in such a manner that an arylamine compound of the above formula (I) is dissolved in a suitable solvent together with a binder, and as the case requires, a suitable carrier-generating material, a sensitizing dye, an electron attracting compound, other carrier-transporting material, or a conventional additive such as a plasticizer or pigment, is added to obtain a coating solution, which is then coated and dried on a conductive substrate to form a photosensitive layer usually having a film thickness of from a few μm to a few tens μm. In a case of a photosensitive layer comprising two layers i.e. a carrier generation layer and a carrier transport layer, the photoreceptor may be prepared either by coating the above coating solution on a carrier generation layer, or forming a carrier generation layer on a carrier transport layer obtained by coating the above coating solution.

The solvent for the preparation of the coating solution may be a solvent which is capable of dissolving the arylamine compound, for example, an ether such as tetrahydrofuran or 1,4-dioxane; a ketone such as methyl ethyl ketone or cyclohexanone; an aromatic hydrocarbon such as toluene or xylene; an aprotic polar solvent such as N,N-dimethylformamide, acetonitrile, N-methylpyrrolidone or dimethylsulfoxide; an ester such as ethyl acetate, methyl formate or methyl cellosolve acetate; or a chlorinated hydrocarbon such as dichloroethane or chloroform. Of course, it is necessary to select the one which is capable of dissolving the binder, among these solvents.

The binder resin to be used for the carrier transport layer in the case of a lamination type photosensitive layer or the binder resin to be used as a matrix in the case of a dispersion type photosensitive layer is preferably a polymer which has good compatibility with the carrier transport material and which is free from phase separation or crystallization of the carrier-transporting material after formation of a coating film. For example, it may be a polymer or copolymer of a vinyl compound such as styrene, vinyl acetate, vinyl chloride, an acrylic acid ester, a methacrylic acid ester or butadiene, or various polymers such as polyvinyl acetal, polycarbonate, polyester, polyester carbonate, polysulfone, polyimide, polyphenylene oxide, polyurethane, cellulose ester, cellulose ether, a phenoxy resin, a silicon resin or an epoxy resin. Further, their partially crosslinked cured products may also be used. The binder is used usually in an amount of from 0.5 to 30 times by weight, preferably from 0.7 to 10 times by weight, relative to the arylamine compound.

In a photosensitive layer containing the arylamine compound of the formula (I) and the pyrenehydrazone compound of the formula (X), in the case of a lamination type photosensitive layer, the carrier transport layer consists essentially of a binder resin, the arylamine compound of the formula (I) and the pyrenehydrazone compound of the formula (X), and in the case of a dispersion-type photosensitive layer, the above-mentioned carrier-generating material is dispersed in a matrix comprising a binder resin and the compounds of the formulas (I) and (X) as main components.

In such a case, the binder resin is used in an amount of from 0.5 to 3.3 times by weight, preferably from 0.66 to 2.5 times by weight, to the total amount of the compounds of the formulas (I) and (X). The compound of the formula (I) is preferably used in an amount of at least 20% by weight in the carrier transport layer in the case of the lamination-type or in the photosensitive layer in the case of the dispersion-type. However, in order to obtain a higher effect, it is more preferably used within a range of from 25 to 45% by weight.

In the case of a lamination-type photosensitive layer, the carrier transport layer may further contain various additives such as an antioxidant and a sensitizer and other carrier-transporting material. The thickness of the carrier transport layer is usually from 10 to 60 μm, preferably from 10 to 45 μm, more preferably from 27 to 40 μm. As the outermost layer, a conventional overcoat layer made essentially of e.g. a thermoplastic or thermosetting polymer, may be provided. Usually, the carrier transport layer is formed on the carrier generation layer, but the reverse arrangement is possible. As a method for forming the respective layers, a conventional method may be employed such that coating solutions obtained by dissolving or dispersing in solvents the substances to be incorporated in the respective layers, are sequentially coated. The carrier transport layer may further contain various additives to improve the mechanical strength or the durability of the coating layer. Such additives include conventional plasticizers, various stabilizers, fluidity-imparting agents and crosslinking agents.

The coating method for the photosensitive layer may, for example, be a spray coating method, a spiral coating method, a ring coating method or a dip coating method.

The spray coating method includes, air spraying, airless spraying, electrostatic air spraying, electrostatic airless spraying, rotary mist-forming electrostatic spraying, hot spraying and hot airless spraying. In consideration of deposition efficiency and fine particle formation in order to obtain a uniform film thickness, it is preferred to employ a rotary mist-forming electrostatic spraying and a transporting method disclosed in republished Japanese PCT Publication No. 805198/1989, i.e. while rotating a cylindrical work, sprayed particles are continuously transported without interruption in its axial direction, whereby an electrophotographic photoreceptor excellent in the uniformity of the film thickness can be obtained in a high overall deposition efficiency.

The spiral coating method may, for example, be a method of using a liquid-injecting coating machine or a curtain coating machine as disclosed in Japanese Unexamined Patent Publication No. 119651/1977, a method of continuously jetting a coating material in the form of a string from a fine opening as disclosed in Japanese Unexamined Patent Publication No. 231966/1969, or a method of using multi nozzles as disclosed in Japanese Unexamined Patent Publication No. 193161/1991.

Now, the dip coating method will be described.

Using the arylamine compound of the above formula (I), a binder and a solvent, a coating solution for forming a carrier transport layer is prepared so that the total solid content is preferably at least 25%, more preferably at most 40%, and the viscosity is usually from 50 to 300 centipoise, preferably from 100 to 200 centipoise. Here, the viscosity of the coating solution is determined substantially by the type of the binder polymer and the molecular weight. However, if the molecular weight is low, the mechanical strength of the polymer itself tends to be low. Accordingly, it is preferred to use a binder polymer having a molecular weight not to impair the mechanical strength. Using the coating solution thus prepared, a carrier transport layer is formed by a dip coating method.

Thereafter, the coated layer is dried. Here, it is preferred to control the drying temperature and time so that necessary and adequate drying can be conducted. The drying temperature is usually within a range of from 100° to 250° C., preferably from 110° to 170° C., more preferably from 120° to 140° C. For the drying method, a dry air dryer, a steam dryer, an infrared ray dryer and a far infrared ray dryer, may be employed.

The electrophotographic photoreceptor of the present invention has a feature that the sensitivity is very high, the residual potential which causes fogging, is small, and light fatigue is little, whereby it is excellent in the durability with no substantial accumulation of the residual potential and no substantial change in the surface potential and the sensitivity.

Now, the present invention will be described in further detail with reference to Examples. However, it should be understood that the present invention is by no means restricted to such specific Preparation Examples and Working Examples. In the following Examples, "parts" means "parts by weight".

PREPARATION EXAMPLE 1

10 g of bis(p-diphenylaminophenoxy)methane of the formula:

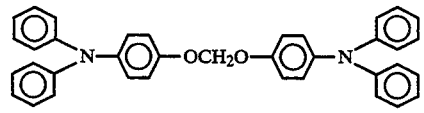

was dissolved in 100 ml of N,N-dimethylformamide, and then 7.0 ml of phosphorus oxychloride was added thereto. The mixture was then reacted at 65° C. for 10 hours.

After cooling, the reaction solution was put into 200 g of ice water and hydrolyzed with sodium hydroxide, followed by extraction, concentration and purification treatments by conventional methods to obtain 6.1 g of a known bisformyl compound of the following formula as a yellow oil:

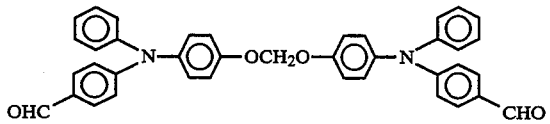

PREPARATION EXAMPLE 2

3.3 g Of the bisformyl compound prepared in Preparation Example 1 and 6.8 g of diethyldiphenylmethyl phosphonate were dissolved in 55 ml of 1,2-dimethoxyethane. Then, 1.1 g of 50% sodium hydride was gradually added thereto. Then, the mixture was refluxed under heating for 7 hours.

After cooling, the reaction solution was put into 200 g of ice water, followed by extraction, concentration and purification treatments by conventional methods to obtain 2.7 g of slightly yellow crystals (melting point: 110°–112° C.). This compound was found to be an arylamine compound of the above identified formula of Compound No. A-21 from the following results of the elemental analysis and the infrared absorption spectrum (FIG. 1).

| Elemental analysis: as $C_{65}H_{50}N_2O_2$ | | | |
|---|---|---|---|
| | C % | H % | N % |
| Calculated | 87.61 | 5.66 | 3.14 |
| Found | 87.90 | 5.69 | 3.01 |

Results of mass spectrometry: as $C_{65}H_{50}N_2O_2$, MW=890 M+=890

PREPARATION EXAMPLE 3

3.3 g of the bisformyl compound prepared in preparation Example 1 and 6.1 g of 9-dimethylphosphonylfluorene were dissolved in 55 ml of 1,2-dimethoxyethane. Then, 1.1 g of 50% sodium hydride was gradually added thereto. The mixture was then refluxed under heating for 7 hours.

After cooling, the reaction solution was put into 200 g of ice water, followed by extraction, concentration and purification treatments by conventional methods to obtain 2.9 g of yellow crystals (melting point: 126°–128° C.).

Figure 2:
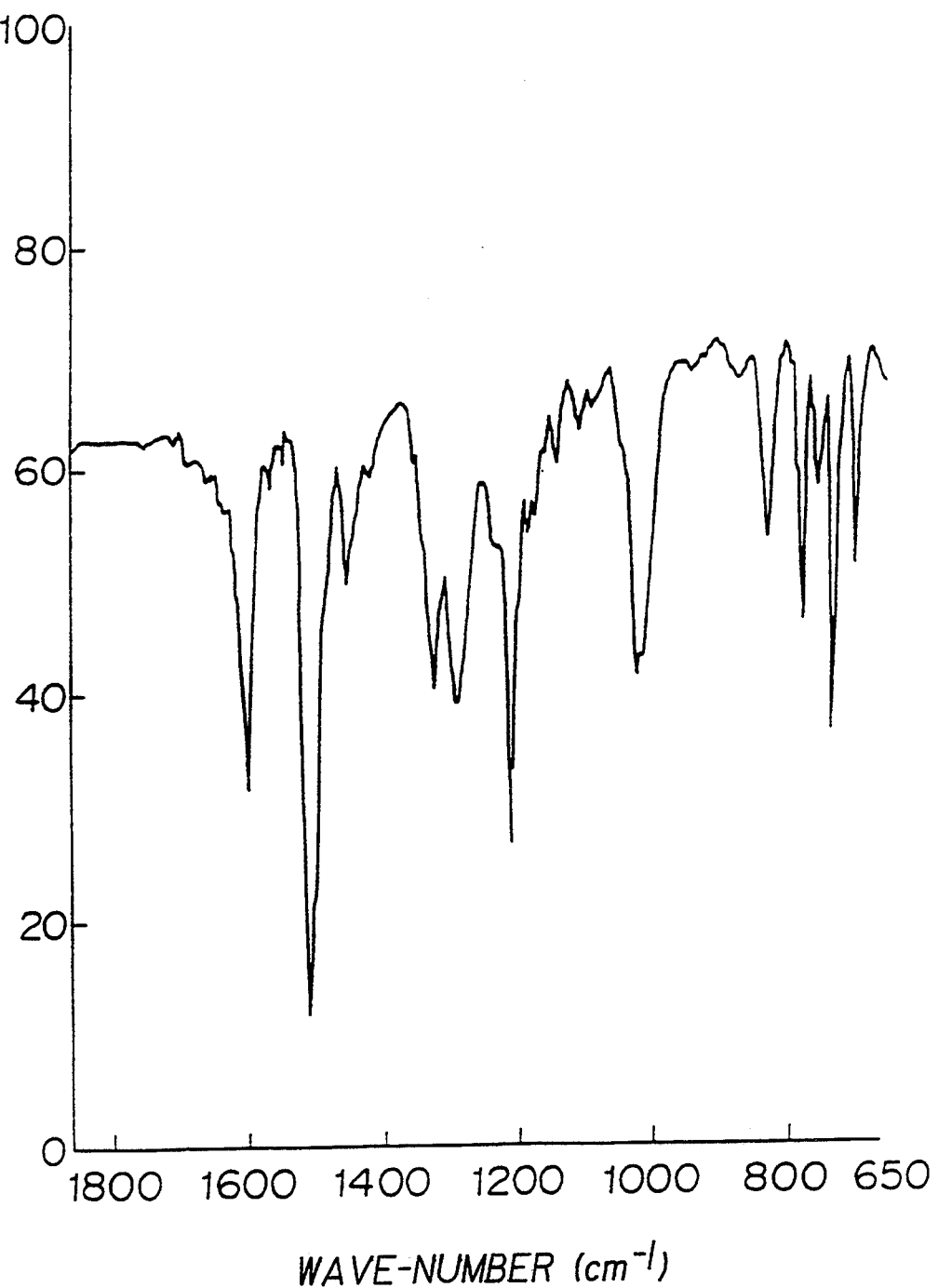
FIG. 2 shows an infrared absorption spectrum of the arylamine compound obtained in Preparation Example 3.

This compound was found to be an arylamine compound of the above-mentioned formula of Compound No. A-54 from the following results of the elemental analysis and the infrared absorption spectrum (FIG. 2).

| Elemental analysis: as $C_{65}H_{46}N_2O_2$ | | | |
|---|---|---|---|
| | C % | H % | N % |
| Calculated | 88.01 | 5.23 | 3.16 |
| Found | 87.93 | 5.29 | 3.14 |

Results of mass spectrometry: as $C_{65}H_{46}N_2O_2$, MW=886 M+=886

PREPARATION EXAMPLE 4

Preparation of an oxytitanium phthalocyanine used in e.g. Example 51

97.5 g of phthalodinitrile was added to 750 ml of α-chloronaphthalene. Then, 22 ml of titanium tetrachloride was dropwise added thereto under a nitrogen atmosphere. After the dropwise addition, the temperature was raised, and the mixture was reacted at a temperature of from 200° to 220° C. for 3 hours under stirring and then left to cool. The mixture was filtered while it was still hot at a temperature of from 100° to 130° C. and washed with 200 ml of α-chloronaphthalene heated to 100° C. The obtained crude cake was suspended and washed at room temperature with 300 ml of α-chloronaphthalene and then with 300 ml of methanol. Further, hot suspension washing with 800 ml of methanol for one hour was repeated a few times. The obtained cake was suspended in 700 ml of water, and hot suspension washing was conducted for 2 hours.

The pH of the filtrate was not higher than 1. Hot water suspension washing was repeated until the pH of the filtrate became from 6 to 7.

The X-ray diffraction spectrum of the obtained oxytitanium phthalocyanine shows a sharp peak at a Bragg angle (2θ±0.2°) of 27.3°, but other peaks are relatively wide peaks.

EXAMPLE 1

1.0 Part of titanium oxyphthalocyanine pigment was added to 14 parts of dimethoxyethane, and the mixture was dispersed and pulverized by a sand grinders. Then, 14 parts of dimethoxyethane and 14 parts of 4-methoxy-4-methylpentanone-2 (manufactured by Mitsubishi Kasei Corporation) were added thereto and diluted. Further, the mixture was mixed with a solution obtained by dissolving 0.5 part of polyvinyl butyral (Denka Butyral #6000-C, trade name, manufactured by Denki Kagaku Kogyo K.K.) and 0.5 part of a phenoxy resin (UCAR ® PKHH, manufactured by Union Carbide) in a solvent mixture comprising 6.6 parts of dimethoxyethane and 6 parts of 4-methoxy-4-methylpentanone-2, to obtain a dispersion. This dispersion was coated on an aluminum layer vapor deposited on a polyester film having a thickness of 75 μm, by a wire bar so that the weight after drying would be 0.4 g/m² and then dried to form a carrier generation layer.

On this carrier generation layer, a coating solution prepared by dissolving 70 parts of the arylamine compound (No. A-21) prepared in Preparation Example 2 and 100 parts of a polycarbonate resin of the following formula (the following formula shows that the polycarbonate resin is a copolymer polycarbonate comprising two types of structural units, and the ratio of these structural units in the copolymer polycarbonate is 1:1):

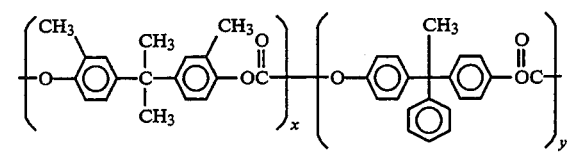

x:y = 1:1 in a solvent mixture comprising 585 parts of tetrahydrofuran and 315 parts of dioxane, was coated and dried to form a carrier transport layer having a thickness of 17 μm.

With respect to the electrophotographic photoreceptor having a photosensitive layer comprising the two layers thus formed, the sensitivity i.e. the half value exposure was measured and found to be 0.36 (μJ/cm²) and the residual potential was 17 V.

The half value exposure was determined in such a manner that firstly, the photoreceptor was charged with a corona current of 50 μA in a dark place and then subjected to exposure with a light of 780 nm, whereby the exposure required for attenuation of the surface potential from 450 V to 225 V was measured.

EXAMPLE 2

A photoreceptor was prepared in the same manner as in Example 1 except that a naphthalic acid-type bisazo pigment of the following formula was used instead of the naphthalocyanine pigment used in Example 1. The photoreceptor was subjected to exposure with white light, and the half value exposure was measured and found to be 0.75 lux.sec and the residual potential was 0 V.

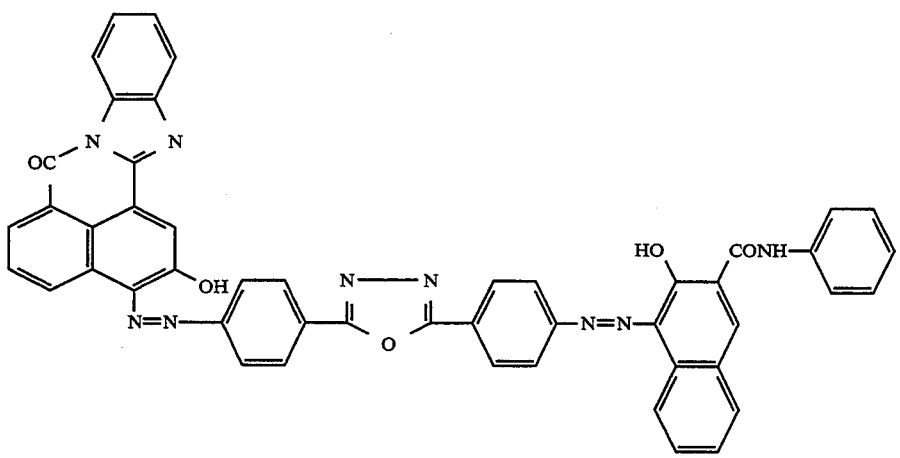

EXAMPLES 3 to 10

The sensitivity of the electrophotographic photoreceptor prepared in the same manner as in Example 1 except that the arylamine compound identified in the following Table 1 prepared in the same manner as in Preparation Example 2 was used instead of the arylamine compound used in Example 1, is shown in Table 1.

TABLE 1

| Example No. | Compound No. | Sensitivity ($\mu J/cm^2$) |
| --- | --- | --- |
| 3 | A-1 | 1.10 |
| 4 | A-3 | 0.48 |
| 5 | A-5 | 0.47 |
| 6 | A-11 | 0.59 |
| 7 | A-19 | 0.34 |
| 8 | A-32 | 0.35 |
| 9 | A-40 | 0.37 |
| 10 | A-41 | 0.76 |

EXAMPLES 11 to 18

The sensitivity of the electrophotographic photoreceptor prepared in the same manner as in Example 2 except that the arylamine compound identified in the following Table 2 prepared in the same manner as in Preparation Example 2 was used instead of the arylamine compound used in Example 1, is shown in Table 2.

TABLE 2

| Example No. | Compound No. | Sensitivity (lux · sec) |
| --- | --- | --- |
| 11 | A-1 | 2.30 |
| 12 | A-3 | 1.00 |
| 13 | A-5 | 0.96 |
| 14 | A-11 | 1.34 |
| 15 | A-19 | 0.72 |
| 16 | A-32 | 0.72 |
| 17 | A-40 | 0.75 |
| 18 | A-41 | 1.51 |

EXAMPLE 19

An electrophotographic photoreceptor was prepared in the same manner as in Example 1 except that the arylamine compound (No. A-54) prepared in Preparation Example 3 was used instead of the arylamine compound used in Example 1.

The electrophotographic photoreceptor thus obtained was subjected to exposure with a light of 780 nm, and the half value exposure was measured and found to be 0.38 $\mu J/cm^2$.

EXAMPLE 20

A photoreceptor was prepared in the same manner as in Example 19 except that the same naphthalic acid type bisazo pigment as used in Example 2 was used instead of the phthalocyanine pigment used in Example 19. The photoreceptor was subjected to exposure with white light, and the half value exposure was measured and found to be 0.77 lux.sec.

EXAMPLES 21 to 28

The sensitivity of the electrophotographic photoreceptor prepared in the same manner as in Example 19 except that the arylamine compound as identified in the following Table 3 prepared in the same manner as in Preparation Example 3 was used instead of the arylamine compound used in Example 19, is shown in Table 3.

TABLE 3

| Example No. | Compound No. | Sensitivity ($\mu J/cm^2$) |
| --- | --- | --- |
| 21 | A-42 | 0.68 |
| 22 | A-43 | 0.55 |
| 23 | A-52 | 0.44 |
| 24 | A-53 | 0.41 |
| 25 | A-55 | 0.39 |
| 26 | A-56 | 0.47 |
| 27 | A-61 | 0.50 |
| 28 | A-63 | 0.45 |

EXAMPLES 29 to 36

The sensitivity of the electrophotographic photoreceptor prepared in the same manner as in Example 20 except that the arylamine compound as identified in the following Table 4 prepared in the same manner as in Preparation Example 3 was used instead of the arylamine compound used in Example 20, is shown in Table 4.

TABLE 4

| Example No. | Compound No. | Sensitivity (lux · sec) |
| --- | --- | --- |
| 29 | A-42 | 1.40 |
| 30 | A-43 | 1.15 |

TABLE 4-continued

| Example No. | Compound No. | Sensitivity (lux · sec) |
|---|---|---|
| 31 | A-52 | 0.89 |
| 32 | A-53 | 0.85 |
| 33 | A-55 | 0.80 |
| 34 | A-56 | 0.92 |
| 35 | A-61 | 1.03 |
| 36 | A-63 | 0.95 |

EXAMPLE 37

1.0 Part of the same naphthalic acid type bisazo pigment as used in Example 2 was added to 14 parts of dimethoxyethane, and the mixture was pulverized by a sand grinder. Then, 14 parts of dimethoxyethane and 14 parts of 4-methoxy-4-methylpentanone-2 (manufactured by Mitsubishi Kasei Corporation) were added thereto and diluted. Further, the mixture was mixed with a solution prepared by dissolving 0.5 part of polyvinyl butyral (Denka Butyral #6000-C, trade name, manufactured by Denki Kagaku Kogyo K.K.) and 0.5 part of a phenoxy resin (UCAR ® PKHH, manufactured by Union Carbide) in a solvent mixture comprising 6.6 parts of dimethoxyethane and 6 parts of 4-methoxy-4-methylpentanone-2, to obtain a dispersion. This dispersion was coated on an aluminum layer vapor deposited on a polyester film having a thickness of 75 μm, by a wire bar so that the weight after drying would be 0.4 g/m² and then dried to form a carrier generation layer.

On this carrier generation layer, a coating solution prepared by dissolving 110 parts of the arylamine compound No. A-21 and 100 parts of the same polycarbonate resin as used in Example 1 in a solvent mixture comprising 302 parts of tetrahydrofuran and 163 parts of dioxane, was coated and dried to form a carrier transport layer having a thickness of 40 μm.

The electron photographic photoreceptor having a photosensitive layer comprising the two layers thus formed, was mounted on a photoreceptor property measuring apparatus (Model EPA-8100, manufactured by Kawaguchi Denki K.K.) and charged so that the flow-in current to the aluminum surface would be 72 μA, followed by exposure and discharge, whereby the half value exposure sensitivity (E½, standard potential: 700 V) and the residual potential (Vr) were measured. The results were good with a half value exposure sensitivity of 0.84 (lux.sec) and a residual potential of 8 V, and the chargeability and the response speed at a low temperature were also excellent. The running properties in an actual copying operation were good, and even after copying 30,000 sheets, the residual potential did not increase, and the stability was maintained.

EXAMPLE 38

With respect to the photoreceptor prepared in the same manner as in Example 37 except that a naphthalic acid type bisazo pigment of the following formula was used instead of the naphthalic acid type bisazo pigment used in Example 37, the electrical properties were measured in the same manner as in Example 37, whereby the half value exposure sensitivity was 1.09 lux.sec and the residual potential was 7 V, and the chargeability under a low temperature condition was particularly good.

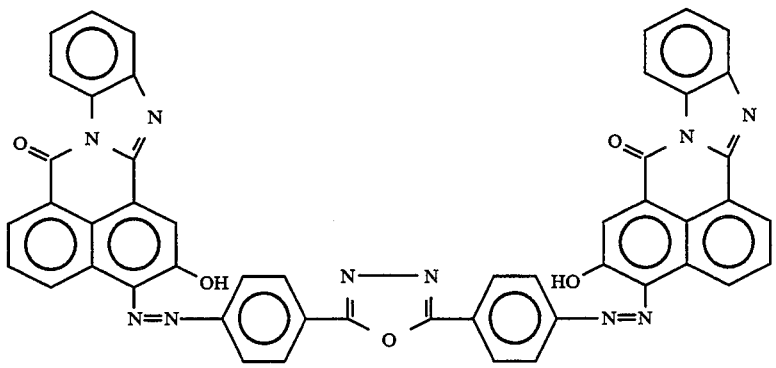

EXAMPLES 39 to 44

The sensitivity and the residual potential of the electrophotographic photoreceptor prepared in the same manner as in Example 37 except that the arylamine compound identified in the following Table 5 was used instead of the arylamine compound used in Example 37, are shown in Table 5.

TABLE 5

| Example No. | Compound No. | Sensitivity (lux · sec) (E½) | Residual potential (V) (Vr) |
|---|---|---|---|
| 39 | A-19 | 0.79 | 9 |
| 40 | A-18 | 0.76 | 8 |
| 41 | A-20 | 0.79 | 2 |
| 42 | A-33 | 0.95 | 8 |
| 43 | A-30 | 0.93 | 20 |
| 44 | A-31 | 0.93 | 9 |

EXAMPLES 45 to 50

The sensitivity and the residual potential of the electrophotographic photoreceptor prepared in the same manner as in Example 38 except that the arylamine compound identified in the following Table 6 was used instead of the arylamine compound used in Example 38, are shown in Table 6.

TABLE 6

| Example No. | Compound No. | Sensitivity (lux · sec) (E½) | Residual potential (V) (Vr) |
|---|---|---|---|
| 45 | A-19 | 1.03 | 8 |
| 46 | A-18 | 0.99 | 7 |
| 47 | A-20 | 1.03 | 1 |
| 48 | A-33 | 1.24 | 7 |
| 49 | A-30 | 1.21 | 18 |

TABLE 6-continued

| Example No. | Compound No. | Sensitivity (lux · sec) ($E_{\frac{1}{2}}$) | Residual potential (V) (Vr) |
|---|---|---|---|
| 50 | A-31 | 1.21 | 8 |

EXAMPLE 51

1.0 Part of the same oxytitanium phthalocyanine as prepared in Preparation Example 4 was added to 14 parts of dimethoxyethane, and the mixture was pulverized by a sand grinder. Then, 14 parts of dimethoxyethane and 14 parts of 4-methoxy-4-methylpentanone-2 (manufactured by Mitsubishi Kasei Corporation) were added thereto and diluted. Further, the mixture was mixed with a solution prepared by dissolving 0.5 part of polyvinyl butyral (Denka Butyral #6000-C, trade name, manufactured by Denki Kagaku Kogyo K.K.) and 0.5 part of a phenoxy resin (UCAR® PKHH, manufactured by Union Carbide) in a solvent mixture comprising 6.6 parts of dimethoxyethane and 6 parts of 4-methoxy-4-methylpentanone-2, to obtain a dispersion. This dispersion was coated on an aluminum layer vapor deposited on a polyester film having a thickness of 75 μm by a wire bar so that the weight after drying would be 0.4 g/m² and then dried to form a carrier generation layer.

On this carrier generation layer, a coating solution prepared by dissolving 70 parts of the arylamine compound of the formula of Compound No. A-21 and 100 parts of the same polycarbonate resin as used in Example 1 in a solvent mixture comprising 585 parts of tetrahydrofuran and 315 parts of dioxane, was coated and dried to form a carrier transport layer having a thickness of 17 μm.

The electrophotographic photoreceptor having a photosensitive layer comprising the two layers, was subjected to exposure with a light of 780 nm, and the half value exposure was measured and found to be 0.18 μJ/cm².

EXAMPLES 52 to 59

An electrophotographic photoreceptor was prepared in the same manner as in Example 51 except that the arylamine compound identified in the following Table 7 was used instead of the arylamine compound used in Example 51. The sensitivity of such an electrophotographic photoreceptor was measured in the same manner as in Example 51, and the results are shown in Table 7.

TABLE 7

| Example No. | Compound No. | Sensitivity (μJ/cm²) |
|---|---|---|
| 52 | A-19 | 0.18 |
| 53 | A-18 | 0.20 |
| 54 | A-20 | 0.19 |
| 55 | A-25 | 0.17 |
| 56 | A-33 | 0.20 |
| 57 | A-30 | 0.18 |
| 58 | A-31 | 0.20 |
| 59 | A-41 | 0.20 |

EXAMPLES 60 to 68

An electrophotographic photoreceptor was prepared in the same manner as in Example 51 except that 0.5 part of the same oxytitanium phthalocyanine as used in Example 51 and 0.5 part of an oxytitanium phthalocyanine showing main diffraction peaks at Bragg angles (2θ±0.2°) of 9.3°, 13.2°, 26.2° and 27.1° were used instead of 1.0 part of the oxytitanium phthalocyanine used in Example 51. The sensitivity of such an electrophotographic photoreceptor was measured in the same manner as in Example 51, and the results are shown in Table 8.

TABLE 8

| Example No. | Compound No. | Sensitivity (μJ/cm²) |
|---|---|---|
| 60 | A-21 | 0.26 |
| 61 | A-19 | 0.28 |
| 62 | A-18 | 0.26 |
| 63 | A-20 | 0.28 |
| 64 | A-25 | 0.29 |
| 65 | A-33 | 0.28 |
| 66 | A-30 | 0.30 |
| 67 | A-31 | 0.29 |
| 68 | A-41 | 0.29 |

EXAMPLES 69 to 74

An electrophotographic photoreceptor was prepared in the same manner as in Example 51 except that 0.3 part of the same oxytitanium phthalocyanine as used in Example 51 and 0.7 part of a dichloro tin phthalocyanine showing main diffraction peaks at Bragg angles (2θ±0.2°) of 8.5°, 12.2°, 13.8°, 16.9°, 22.4°, 28.4° and 30.1° were used instead of 1.0 part of the oxytitanium phthalocyanine used in Example 51. The sensitivity of such an electrophotographic photoreceptor was measured in the same manner as in Example 51, and the results are shown in Table 9.

TABLE 9

| Example No. | Compound No. | Sensitivity (μJ/cm²) |
|---|---|---|
| 69 | A-21 | 0.29 |
| 70 | A-18 | 0.30 |
| 71 | A-20 | 0.28 |
| 72 | A-33 | 0.30 |
| 73 | A-31 | 0.30 |
| 74 | A-30 | 0.28 |

EXAMPLE 75

10 parts by weight of the same bisazo compound as used in Example 2 was added to 150 parts by weight of 4-methoxy-4-methylpentanone-2 and subjected to pulverization and dispersion treatment by a sand grind mill. The pigment dispersion thereby obtained was added to a 5% 1,2-dimethpxyethane solution of polyvinyl butyral (#6000-C, trade name, manufactured by Denki Kagaku Kogyo K.K.) to obtain a dispersion having a final solid content concentration of 4.0%.

In the dispersion thus obtained, an aluminum cylinder having an outer diameter of 80 mm, a length of 340 mm and a wall thickness of 1.0 mm and having the surface mirror-finished, was subjected to dip coating to form a carrier generation layer having a film thickness after drying of 0.4 g/m².

Then, a solution prepared by dissolving 88 parts by weight of an arylamine compound (Compound No. A-21), 22 parts of 1-pyrenecarbaldehyde diphenyl hydrazone (Compound No. B-4), 100 parts by weight of a polycarbonate resin (viscosity average molecular weight: 22,000) of the following formula:

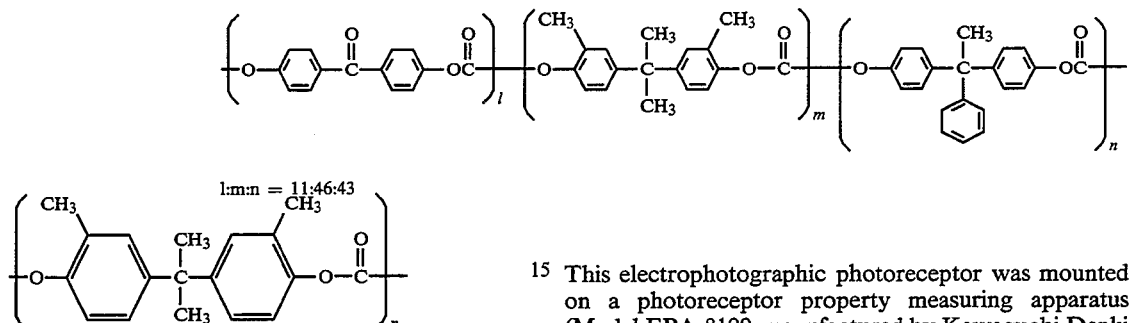

and 1.5 parts of 4-(2,2-dicyanovinyl)phenyl-2,4,5-trichlorobenzenesulfonate in a solvent mixture comprising 1,4-dioxane and tetrahydrofuran, was coated on the carrier generation layer by dip coating and then dried at room temperature for 30 minutes and at 125° C. for 30 minutes to form a carrier transport layer having a thickness after drying of 35 μm. The photoreceptor A thus prepared was mounted on a photoreceptor property measuring apparatus and electrified so that the surface potential would be −700 V, whereby the sensitivity was high with a half value exposure sensitivity $E_{\frac{1}{2}}$ of 0.66 (lux.sec), and the residual potential was as low as 8 V. The durability test was repeated by a commercially available copying machine having a blade cleaning function, whereby even after copying 100,000 sheets, no change was observed in the image quality with no substantial decrease in the potential, although a slight increase in the residual potential was observed.

EXAMPLE 76

A photoreceptor B was prepared and evaluated in the same manner as in Example 75 except that the amount of the arylamine compound (Compound No. A-21) was changed to 70 parts by weight and the amount of 1-pyrenecarbaldehyde diphenyl hydrazone (Compound No. B-4) was changed to to 40 parts by weight. The sensitivity was high with a half value exposure sensitivity $E_{\frac{1}{2}}$ of 0.66 (lux.sec), and the residual potential was as low as 10 V. The results of the repeated durability test were excellent as in Example 75.

EXAMPLE 77

A photoreceptor C was prepared and evaluated in the same manner as in Example 75 except that the amount of the arylamine compound (Compound No. A-21) was changed to 55 parts by weight and the amount of 1-pyrenecarbaldehyde diphenyl hydrazone (Compound No. B-4) was changed to 55 parts by weight. The sensitivity was high with a half value exposure sensitivity $E_{\frac{1}{2}}$ of 0.67 (lux.sec), and the residual potential was as low as 11 V. The results of the repeated durability test were excellent as in Example 75.

EXAMPLE 78

An electrophotographic photoreceptor was prepared in the same manner as in Example 37 except that a polycarbonate resin of the following formula (the following formula indicates that the polycarbonate resin is a copolymer polycarbonate comprising three types of structural units, and the ratios of these structural units in the copolymer polycarbonate are represented by the following numerical values) was used instead of the polycarbonate resin used in Example 37:

This electrophotographic photoreceptor was mounted on a photoreceptor property measuring apparatus (Model EPA-8100, manufactured by Kawaguchi Denki K.K.) and electrified so that the flow-in current to the aluminum surface would be 72 μA, followed by exposure and discharge, whereby the half value exposure sensitivity ($E_{\frac{1}{2}}$, standard potential: 700 V) and the residual potential (Vr) were measured. As a result, the half value exposure sensitivity Was 0.85 (lux.sec), and the residual potential was 9 V.

EXAMPLES 79 to 84

The sensitivity and the residual potential of an electrophotographic photoreceptor prepared in the same manner as in Example 78 except that an arylamine compound identified in the following Table 10 was used instead of the arylamine compound (Compound No. A-21) used in Example 78, are shown in Table 10.

TABLE 10

| Example No. | Compound No. | Sensitivity (lux · sec) ($E_{\frac{1}{2}}$) | Residual potential (V) (Vr) |
|---|---|---|---|
| 79 | A-19 | 0.79 | 10 |
| 80 | A-18 | 0.77 | 9 |
| 81 | A-20 | 0.80 | 4 |
| 82 | A-33 | 0.96 | 9 |
| 83 | A-30 | 0.93 | 21 |
| 84 | A-31 | 0.94 | 10 |

EXAMPLE 85

A photoreceptor was prepared in the same manner as in Example 78 except that the same naphthalic acid bisazo pigment as used in Example 38 was used instead of the naphthalic acid bisazo type pigment used in Example 78, and the electrical properties were measured in the same manner as in Example 78, whereby the half value exposure sensitivity was 1.10 lux.sec, and the residual potential was 8 V.

EXAMPLES 86 to 91

The sensitivity and the residual potential of an electrophotographic photoreceptor prepared in the same manner as in Example 85 except that an arylamine compound identified in the following Table 11 was used instead of the arylamine compound (Compound No. A-21) used in Example 78, are shown in Table 11.

TABLE 11

| Example No. | Compound No. | Sensitivity (lux · sec) ($E_{\frac{1}{2}}$) | Residual potential (V) (Vr) |
|---|---|---|---|
| 86 | A-19 | 1.04 | 10 |
| 87 | A-18 | 0.99 | 9 |
| 88 | A-20 | 1.04 | 5 |

TABLE 11-continued

| Example No. | Compound No. | Sensitivity (lux · sec) (E½) | Residual potential (V) (Vr) |
|---|---|---|---|
| 89 | A-33 | 1.25 | 9 |
| 90 | A-30 | 1.21 | 19 |
| 91 | A-31 | 1.22 | 10 |

COMPARATIVE EXAMPLE 1

A photoreceptor was prepared in the same manner as in Example 37 except that a compound of the following formula was used instead of the arylamine compound (Compound No. A-21), and the electrical properties were measured in the same manner as in Example 37, whereby the sensitivity (half value exposure) was 0.86 (lux.sec), and the residual potential was as high as 45 V, which is problematic for practical application.

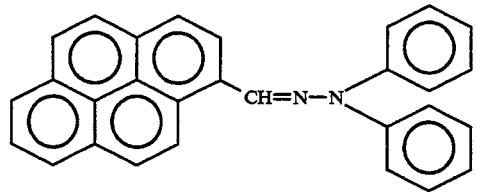

COMPARATIVE EXAMPLE 2

A photoreceptor was prepared in the same manner as in Example 37 except that a compound of the following formula was used instead of the arylamine compound (Compound No. A-21), and the electrical properties were measured in the same manner as in Example 37, whereby the sensitivity (half value exposure) was 0.80 (lux.sec), and the residual potential was extremely high at a level of 120 V, which is problematic for practical application.

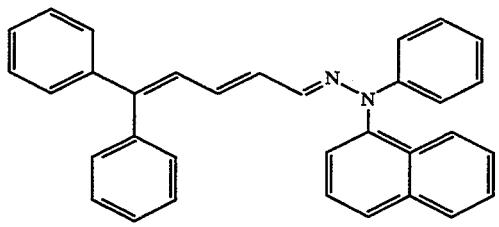

COMPARATIVE EXAMPLE 3

A photoreceptor was prepared in the same manner as in Example 37 except that a compound of the following formula was used instead of the arylamine compound (Compound No. A-21), and the electrical properties were measured in the same manner as in Example 37, whereby the sensitivity (half value exposure) was good at a level of 0.78 (lux.sec), but the residual potential was high at a level of 55 V. Further, with respect to the running properties in an actual copying operation, it had a problem that the residual potential increased with an increase in the number of sheets copied, which is problematic for practical application.

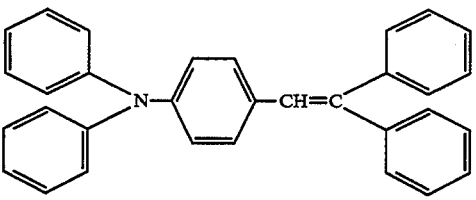

COMPARATIVE EXAMPLE 4

A photoreceptor was prepared in the same manner as in Example 38 except that a compound of the following formula was used instead of the arylamine compound (Compound No. A-21), and the electrical properties were measured in the same manner as in Example 37, whereby the sensitivity (half value exposure) was 1.15(lux.sec), and the residual potential was as high as 43 V, which is problematic for practical application.

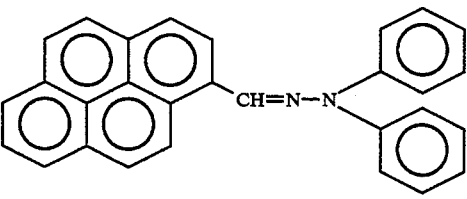

COMPARATIVE EXAMPLE 5

A photoreceptor was prepared in the same manner as in Example 38 except that a compound of the following formula was used instead of the arylamine compound (Compound No. A-21), and the electrical properties were measured in the same manner as in Example 37, whereby the sensitivity (half value exposure) was 1.06 (lux.sec), and the residual potential was very high at a level of 115 V, which is problematic for practical application.

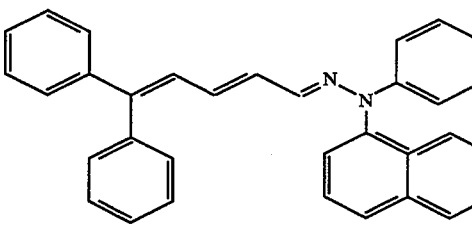

COMPARATIVE EXAMPLE 6

A photoreceptor was prepared in the same manner as in Example 38 except that a compound of the following formula was used instead of the arylamine compound (Compound No. A-21) was used, and the electrical properties were measured in the same manner as in Example 37, whereby the sensitivity (half value exposure) was good at a level of 1.01 (lux.sec), but the residual potential was very high at a level of 120 V. Further, problems for practical application were found with respect to the chargeability at a low temperature, the response speed and the running properties in the actual copying operation.

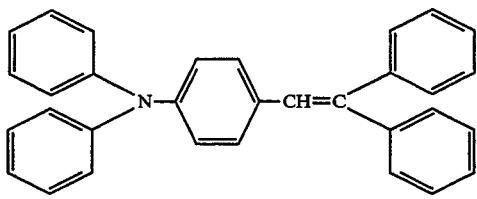

COMPARATIVE EXAMPLE 7

A comparative photoreceptor E was prepared and evaluated in the same manner as in Example 75 except that the amount 1-pyrenecarbaldehyde diphenyl hydrazone (Compound No. B-4) was changed to 110 parts by weight without using the arylamine compound (Compound No. A-21). Both the half value exposure and the repeated durability test results were good, but there was a problem that the residual potential was high.

COMPARATIVE EXAMPLE 8

A photoreceptor was prepared in the same manner as in Example 1, except that a compound of the following formula was used instead of the arylamine compound (Compound No. A-21). The electrical properties were measured in the same manner as in Example 1, whereby the sensitivity (half value exposure) was 5.77 ($\mu$J/cm$^2$), and the residual potential (Vr) was very high at a level of 216 V.

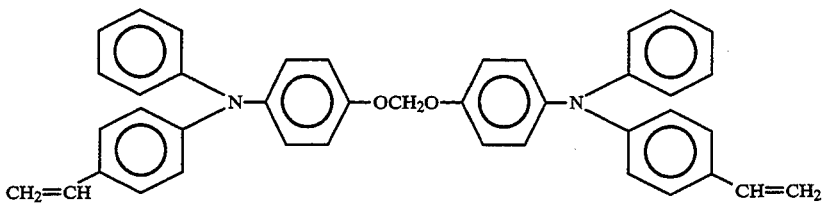

COMPARATIVE EXAMPLE 9

A photoreceptor was prepared in the same manner as in Example 2, except that the same compound as used in Comparative Example 8 was used, and the electrical properties were evaluated in the same manner as in Example 2. As this result, the sensitivity could not be measured since the light decay was insufficient, and the residual potential (Vr) was very high at a level of 431 V.

What is claimed is:

1. An electrophotographic photoreceptor comprising an electrically conductive substrate and a photosensitive layer formed thereon, wherein said photosensitive layer contains an arylamine compound of the following formula (I):

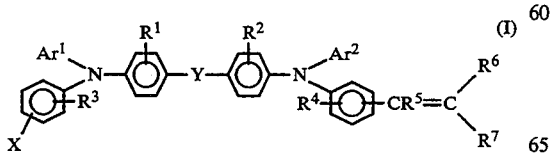

wherein X is a hydrogen atom or a group of the formula (II):

$$-CR^8=C\begin{matrix}R^9\\R^{10}\end{matrix} \quad (II)$$

Y is a group of the formula (III) or (IV):

$$-O-A^1-O- \quad (III)$$

$$-A^2-O-A^3- \quad (IV)$$

wherein $A^1$ in the formula (III) is a bivalent hydrocarbon residue which may have substituents, and each of $A^2$ and $A^3$ in the formula (IV) is an alkylene group which may have substituents, an arylene group which may have substituents, or a group wherein an alkylene group which may have substituents and an arylene group which may have substituents, are bonded, and $A^2$ and $A^3$ may be the same or different from each other; each of $Ar^1$ and $Ar^2$ which may be the same or different, is an alkyl group which may have substituents, an aryl group which may have substituents, or a heterocyclic group which may have substituents; each of $R^1$, $R^2$, $R^3$ and $R^4$ which may be the same or different, is a hydrogen atom, a halogen atom, an alkyl group which may have substituents, an alkoxy group which may have substituents, or a substituted amino group; each of $R^5$, $R^6$, $R^7$, $R^8$, $R^9$ and $R^{10}$ which may be the same or different, is a hydrogen atom, an alkyl group which may have substituents, an aryl group which may have substituents, or a heterocyclic group which may have substituents, or $R^6$ and $R^7$, or $R^9$ and $R^{10}$ are condensed to form a carbon ring group which may have substituents, or a heterocyclic group which may have substituents, provided that with respect to the pair of $R^6$ and $R^7$ and the pair of $R^9$ and $R^{10}$, when one of each pair is a hydrogen atom or an alkyl group, the other is an aryl group or a heterocyclic group.

2. The electrophotographic photoreceptor according to claim 1, wherein the photosensitive layer contains the arylamine compound of the formula (I) and a pyrenehydrazone compound of the following formula (X):

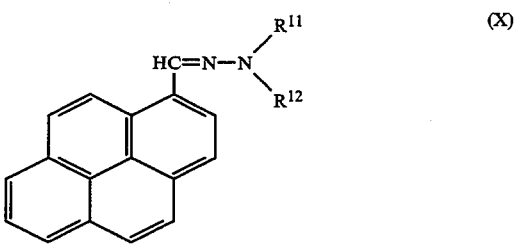

wherein $R^{11}$ is an alkyl group, an allyl group, an aryl group which may have substituents, or an aralkyl group which may have substituents, and $R^{12}$ is an aryl group which may have substituents.

3. The electrophotographic photoreceptor according to claim 1, wherein the photosensitive layer contains the arylamine compound of the formula (I) and oxytitanium phthalocyanine showing a main diffraction peak at a Bragg angle ($2\theta \pm 0.2°$) of 27.3° in the X-ray diffraction spectrum, as a carrier-generating material.

4. The electrophotographic photoreceptor according to claim 1, wherein Y in the formula (I) is a group of the formula (III).

5. The electrophotographic photoreceptor according to claim 1, wherein $A^1$ in the formula (III) is an alkylene group which may have substituents, an arylene group which may have substituents, or a group wherein an alkylene group which may have substituents and a arylene group which may have substituents, are bonded.

6. The electrophotographic photoreceptor according to claim 1, wherein Y in the formula (I) is a group of the formula (IV).

7. The electrophotographic photoreceptor according to claim 1, wherein Y in the formula (I) is a group of the formula (III), and each of $R^5$, $R^6$, $R^7$, $R^8$, $R^9$ and $R^{10}$ which may be the same or different, is a hydrogen atom, an alkyl group which may have substituents, an aryl group which may have substituents, or a heterocyclic group which may have substituents, provided that with respect to the pair of $R^6$ and $R^7$ and the pair of $R^9$ and $R^{10}$, when one of each pair is a hydrogen atom or an alkyl group, the other is an aryl group or a heterocyclic group.

8. The electrophotographic photoreceptor according to claim 1, wherein Y in the formula (I) is a group of the formula (III); and each of $R^5$, $R^6$, $R^7$, $R^8$, $R^9$ $R^{10}$ which may be the same or different, is a hydrogen atom, an alkyl group which may have substituents, an aryl group which may have substituents, or a heterocyclic group which may have substituents, provided that with respect to the pair of $R^6$ and $R^7$ and the pair of $R^9$ and $R^{10}$, when one of each pair is a hydrogen atom or an alkyl group, the other is an aryl group or a heterocyclic group, or $R^6$ and $R^7$, or $R^9$ and $R^{10}$ are condensed to form a carbon ring group which may have substituents, or a heterocyclic group which may have substituents; provided that (1) when X is a hydrogen atom, $R^6$ and $R^7$ are condensed to form the carbon ring group or the heterocyclic group, and (2) when X is a group of the formula (II), at least one of the pairs of $R^6$ and $R^7$, and $R^9$ and $R^{10}$, are condensed to form the carbon ring group or the heterocyclic group.

9. The electrophotographic photoreceptor according to claim 1, wherein the photosensitive layer comprises a carrier generation layer and a carrier transport layer, and the carrier transport layer contains the arylamine compound of the formula (I).

10. The electrophotographic photoreceptor according to claim 2, wherein the blend ratio of the compound of the formula (I) to the compound of the formula (X) is within a range of from 95:5 to 20:80.

11. The electrophotographic photoreceptor according to claim 2, wherein the photosensitive layer comprises a carrier generation layer and a carrier transport layer, and the carrier transport layer contains the arylamine compound of the formula (I) and the pyrenehydrazone compound of the formula (X).

12. The electrophotographic photoreceptor according to claim 3, wherein the photosensitive layer comprises a carrier generation layer and a carrier transport layer, and the carrier generation layer contains the oxytitanium phthalocyanine showing a main diffraction peak at a Bragg angle ($2\theta \pm 0.2°$) of 27.3° in the X-ray diffraction spectrum and the carrier transport layer contains the arylamine compound of the formula (I).

13. The electrophotographic photoreceptor according to claim 9, wherein the thickness of the carrier generation layer is from 0.05 to 5 $\mu$m, and the thickness of the carrier transport layer is from 10 to 60 $\mu$m.

14. The electrophotographic photoreceptor according to claim 1, wherein the photosensitive layer is a dispersion-type photosensitive layer having a thickness of from 5 to 50 $\mu$m.

15. The electrophotographic photoreceptor as claimed in claim 1, wherein Y is a group of formula (III).

16. An electrophotographic photoreceptor as claimed in claim 1, wherein $A^2$ and $A^3$ are each independently either an arylene group which may have substituents or a group wherein an alkylene group which may have substituents and an arylene group which may have substituents are bonded.

* * * * *